(12) United States Patent
Newton et al.

(10) Patent No.: US 7,183,094 B2
(45) Date of Patent: Feb. 27, 2007

(54) BACTERIAL MYCOTHIOL S-CONJUGATE AMIDASE FAMILY

(75) Inventors: Gerald L. Newton, San Diego, CA (US); Yossef Av-Gay, Vancouver (CA); Robert C. Fahey, Del Mar, CA (US)

(73) Assignees: The Regents of the University of California, Oakland, CA (US); The University of British Columbia, Vancouver (CA)

( * ) Notice: Subject to any disclaimer, the term of this patent is extended or adjusted under 35 U.S.C. 154(b) by 342 days.

(21) Appl. No.: 10/427,218

(22) Filed: Apr. 30, 2003

(65) Prior Publication Data

US 2003/0235901 A1 Dec. 25, 2003

Related U.S. Application Data

(62) Division of application No. 09/733,569, filed on Dec. 7, 2000, now abandoned.

(60) Provisional application No. 60/169,503, filed on Dec. 7, 1999.

(51) Int. Cl.
*C12N 9/80* (2006.01)
(52) U.S. Cl. .................. 435/228; 435/230
(58) Field of Classification Search ............... None
See application file for complete search history.

(56) References Cited

OTHER PUBLICATIONS

Cole et al., *Deciphering the biology of Mycobacterium tuberculosis from the complete genome sequence*, Nature 393:537-544 (1998).

Newton et al., *Mycothiol biochemistry*, Arch. Microbiol. 178:388-394 (2002).

Cole et al., Data Base PIR-68, Accession No. H70894 (Jul. 17, 1998).

Cole et al., "Deciphering the Body of *Mycobacterium tuberculosis* from the Complete Genome Sequence," Nature, Jul. 19, 1998, vol. 393, No. 6685, pp. 537-544.

Newton at al., "A Novel Mycothiol-Dependent Detoxification Pathway in Mycobacteria Involving Mycothiol S-Conjugate Amidase," *Biochemistry*, 2000, vol. 39, pp. 10739-10746.

Robinson, K., "Direct Submission", GenBank Database, Accession No. MLU15183, Mar. 9, 1995.

*Primary Examiner*—Nashaat T. Nashed
(74) *Attorney, Agent, or Firm*—DLA Piper US LLP

(57) ABSTRACT

The present invention provides a family of bacterial acyl glucosaminylinositol amidases with amidase activity against S-conjugate amides, particularly mycothiol-derived S-conjugate amides. The invention amidases are characterized by a highly conserved 20 amino acid N-terminal region and four highly conserved histidine-containing regions and by having amidase activity, particularly amide hydrolase activity. The invention further provides methods for using the invention amidases in drug screening assays to determine compounds with antibiotic activity or compounds that inhibit activity or production of endogenous acyl glucosaminyl inositol amidase in bacteria. The invention further provides methods for detoxifying a toxic substance by contacting the toxic substance with an invention amidase, for example, by expression of the amidase under environmental conditions in a bacterium.

4 Claims, 10 Drawing Sheets

Mycothiol, MSH, AcCys-GlcN-Ins,
1- D-*myo*-inosityl-2-( *N*-acetyl- L-cysteinyl)-
amido-2-deoxy- α-D-glucopyranoside FIGURE 1A
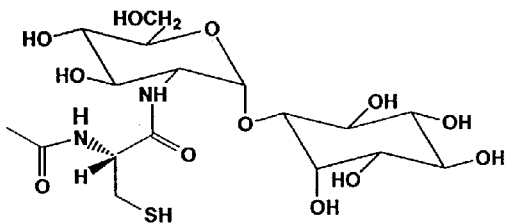
Mycothiol, MSH, AcCys-GlcN-Ins,
1- D-*myo*-inosityl-2-( *N*-acetyl- L-cysteinyl)-
amido-2-deoxy- α-D-glucopyranoside
FIGURE 1B
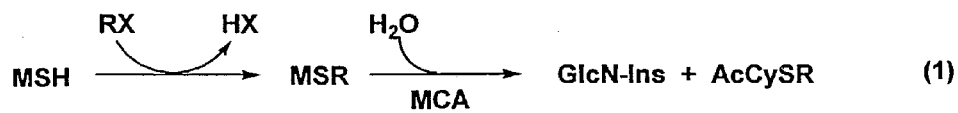
(1)
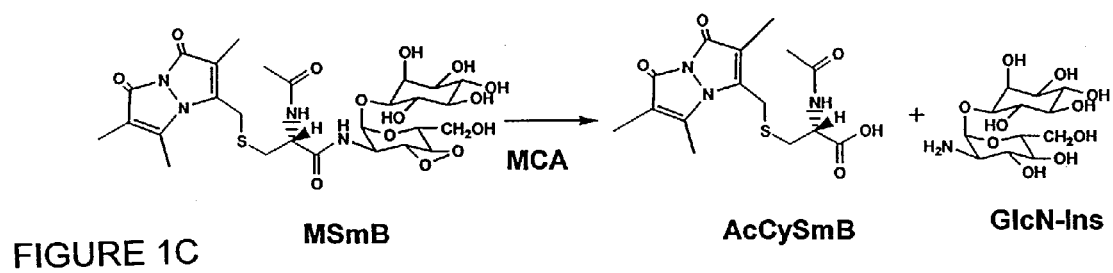
FIGURE 1C

```
Rv1082    1  .VSELRLMAVHAHPDDESSKGAATLARYADEGHRVLVVTLTGGERGEIL..NPAMDLPDV
M.leprae  1  .MSELRLMAVHAHPDDESSKGAATLARYADEGHRVLVVTLTGGERGEIL..NPAMDLPDV
lmbE      1  ..MTQCLLTVHAHPDDEASRGGATVAHYTAQGVRAVLVTCTDGGAGEVL..NPAVTDDFT
rifO      1  ...MGTLVSFHAHPNDDTTTCGGVLRKAHEDGHRVVLVLATRGELGYNP...DGLLAEGET
Rv1170    1  MSETPRLLFVHAHPDDESLSNGATIAHYTSRGAQVHVVTCTLGEEGEVIGDRWAQLTADH Rv1082    58 HGRIAEIRRDEMTKAAEILG.VEHTWLG....FVDSGLPKGDLPPPLPDDCFARVPLEVS
M.leprae  58 HGHIAEIRRDEMAKAAEILG.VEHTWLG....FIDSGLPKGDPPPPLPDDCFALVPLEVC
lmbE      57 PERFVAVRSAELDASARNLGYSAVHRLG....YRDSGMD.G...TAGGAEAFVRAPLDEA
rifO      56 LG...DRRAVEARAAADVLGVDRLEFLG....YTDSGMT....AAADGAGTFQTADVEEA
Rv1170    61 ADQLGGYRIGELTAALRALGVSAPIYLGGAGRWRDSGMAG...TDQRSQRRFVDADPRQT Rv1082    113 TEALVRVVREFRPHVMTTYDENGG.YPHPDHIRCHQVSVAAYEAAGDFCRFPDAGEPWTV
M.leprae  113 TEALVRVVRKFRPHVLTTYDENGG.YPHPDHIRCHQVSVDAYEAACDYRRFPDAGKPWTV
lmbE      109 ATRLARVIADERPDVVIGYGTNHTRDPHPDHIRANEVLTRRVDLLDHTP..........
rifO      105 ARKLAAILREERADVLTVYDEKGT.YGDPDHIQVHRVGTRAAELAGTAK..........
Rv1170    118 VGALVAIIRELRPHVVVTYDPNGG.YGHPDHVHTHTVTTAAVAAAGVGSGTADHPGDPWT Rv1082    172 SKLYYVHGFLRERMQMLQDEFARHGQRGPFEQWLAYWDPDHDFLTSRVTTRVECSKYFSQ
M.leprae  172 SKLYYNHGFLRARMQLLHDEFAKHGQAGPFDKWLAQSNPAHDPFESRVTTRVECSAYFSQ
lmbE      158 ..AVYHIAFSRRRHRALHQACVDSGVPSPYEGGLSAPPGAFDDEWITTLVDVTKGDAVER
rifO      153 ...VFQSTINREHIKANQRVLAEQAG......VDLPAGPDFGTPEAELTCRVDVSAYTEY
Rv1170    177 VPKFYWTVLGLSALISGARALVPDDLRPEWVLPRADEIAFGYSDDGIDAVVEADEQARAA Rv1082    232 RDDALRAHATQIDPNAEFFAAPLAW..QERLWPTEEFELARSRIPAR...PPETELFAGI
M.leprae  232 RDDALRAHATQIDPKAEFFAAPISW..QQRLWPTEEFELARSRVPTR...LPEHDLFAGI
lmbE      216 RLDALRSHVTQVPPASGWFALSPQQ..LRDAFPYEEYTRVG.AAPRE...AVVHDLFTAP
rifO      204 KRKALLAHASQITPQSTLFTDLPED..TFRTMFGTEWFIRAGQGPG....ITETDLMA..
Rv1170    237 KVAALAAHATQVVVGPTGRAAALSNNLALPILADEHYVLAGGSAGARDERGWETDLLAGL Rv1082    287 EP.....
M.leprae  287 EAAG...
lmbE      270 A......
rifO          .......
Rv1170    297 GFTASGT
```

FIGURE 6

```
Rv1082:      1 MSELRLMAVHAHPDDESSKGAATLARYADEGHRVLVVTLTGGERGEILNPAMDLPDVHGR 60
               MSELRLMAVHAHPDDESSKGAAT ARYA EG RV+VVTLTGGERG+ILNPAMDLP+VHGR
M.smeg:33215   MSELRLMAVHAHPDDESSKGAATTARYAAEGARVMVVTLTGGERGDILNPAMDLPEVHGR 33036

Rv1082:     61 IAEIRRDEMTKAAEILGVEHTWLGFVDSGLPKGDLPPPLPDDCFARVPLEVSTEALVRVV 120
               IAE+RRDEM KAAEILGVEH WLGFVDSGLP+GD  PPLPD CFA VPLE    + LVRV+
M.smeg:33035   IAEVRRDEMAKAAEILGVEHHWLGFVDSGLPEGDPLPPLPDGCFALVPLEEPVKRLVRVI 32856

Rv1082:    121 REFRPHVMTTYDENGGYPHPDHIRCHQVSVAAYEAAGDFCRFPDAGEPWTVSKLYYVHGF 180
               REFRPHVMTTYDENGGYPHPDHIRCHQVSVAAYEAA D   +PDAGEPW V KLYY HGF
M.smeg:32855   REFRPHVMTTYDENGGYPHPDHIRCHQVSVAAYEAAADHLLYPDAGEPWAVQKLYYNHGF 32676

Rv1082:    181 LRERMQMLQDEFARHGQRGPFEQWLAYWDPDHDFLTSRVTTRVECSKYFSQRDDALRAHA 240
               LR+RMQ+LQ+EFA++GQ GPF +WL +WDPD+D   +RVTTRV C++YF QRDDALRAHA
M.smeg:32675   LRQRMQLLQEEFAKNGQEGPFAKWLEHWDPDNDVFANRVTTRVHCAEYFHQRDDALRAHA 32496

Rv1082:    241 TQIDPNAEFFAAPLAWQERLWPTEEFELARSRIPARPPETELFAGIEP 288
               TQIDP  +FF AP+ WQ+RLWPTEEFELAR+R+P    PE +LF G+EP
M.smeg:32495   TQIDPKGDFFHAPIEWQQRLWPTEEFELARARVPVTLPEDDLFKGVEP 32352
```

Figure 9

```
Rv1082:    863 GGCTCGATCCCGGCGAACAATTCGGTCTCCGGTGGGCGCG-CGGGGATACGCGAGCGAGC 805
               |||||||  |||   |||||   |||   ||| ||  | | | ||| |  ||   || ||
M.smeg: 32353 GGCTCGACCCCCTTGAACAGGTCGTCCTCGGGCAG-CGTGACCGGCACGCGGGCCCGCGC 32411

Rv1082:    804 CAACTCGAATTCCTCGGTCGGCCACAGCCGCTCCTGCCAGGCAAGCGGGGCGGCGAAGAA 745
               | |||||| |||||||||||||||||| ||||| ||||| | ||  ||||||||  ||||||
M.smeg:  32412 GAGCTCGAACTCCTCGGTCGGCCACAACCGCTGCTGCCACTCGATCGGGGCGTGGAAGAA 32471

Rv1082:    744 TTCGGCGTTCGGGTCGATCTGGGTGGCATGCGCGCGCAACGCATCGTCGCGTTGGCTGAA 685
               ||| | || ||  |||||||| ||  |||||  ||||||||||||| || |||  |||
M.smeg:  32472 GTCGCCCTTGGGATCGATCTGTGTCGCGTGCGCACGCAACGCGTCGTCACGCTGGTGGAA 32531

Rv1082:    684 GTATTTCGAGCACTCGACCCGGGTGGTCACTCGGCTGGTGAGAAAGTCATGGTCGGGGTC 625
               ||| | || ||| |  ||  ||||||||||| |||  ||| || | |||  || || ||
M.smeg: 32532 GTACTCCGCGCAGTGCACGCGGGTGGTCACCCGGTTGGCGAACACGTCGTTGTCGGGATC 32591

Rv1082:    624 CCAGTACGCCAGCCATTGTTCGAATGGGCCGCGTTGGCCGTGCCGGGCGAACTCATCCTG 565
               |||||  |  ||||||   ||||||  || |||||  || ||| | ||||||  ||||||
M.smeg: 32592 CCAGTGCTCGAGCCATTTGGCGAACGGGCCCTCCTGCCCGTTCTTGGCGAACTCCTCCTG 32651

Rv1082:    564 CAACATCTGCATCCGCTCCCGCAGGAAGCCGTGGACGTAGTACAGCTTGGACACCGTCCA 505
               |   |  ||||| |||    || ||||||| |||  ||||||||||||  | |||  ||
M.smeg: 32652 CAGGAGCTGCATGCGCTGACGGAGGAAGCCATGGTTGTAGTACAGCTTCTGCACCGCCCA 32711

Rv1082:    504 CGGCTCACCCGCGTCGGGAAACCGGCAAAAG-TCACCGGCCGCCTCGTAGGCAGCCACCG 446
               |||||||||  |||||||||    |  |  ||   | || ||||||||||  ||||||||
M.smeg: 32712 CGGCTCACCGGCGTCGGGATACAG-CAGGTGGTCGGCCGCGGCCTCGTACGCGGCCACCG 32770

Rv1082:    445 AAACCTGATGGCAGCGAATGTGGTCGGGATGTGGGTAGCCGCCGTTCTCGTCGTAGGTGG 386
               | |||||  |||||||| ||||||||||||||||||| ||||||  || ||||||||||||   ||||
M.smeg: 32771 ACACCTGGTGGCAGCGGATGTGGTCGGGATGCGGGTAACCACCGTTCTCGTCGTACGTGG 32830

Rv1082:    385 TCATCACGTGCGGCCGAAACTCGCGAACCACCCGCACCAG-CGCCTCGGTGGACACCTCC 327
               |||||||||||||  ||||||||||||| | |||||||||||||| |  |   ||  |  ||||
M.smeg: 32831 TCATCACGTGCGGGCGGAACTCGCGGATCACCCGCACCAGACGCTT-GACGGGCTCCTCG 32889

Rv1082:    326 AGCGGTACCCGCGCGAAGCAGTCATCAGGCAGCGGTGGCGGTAAATCACCCTTAGGTAGC 267
               |||||  |||  |  |||||  ||  |  || ||||| ||||   ||||||||   | |
M.smeg: 32890 AGCGGGACCAGGGCGAAACACCCGTCGGGCAGCGGCGGCAGCGGGTCACCCTCCGGCAAT 32949

Rv1082:    266 CCGGAGTCGACGAAGCCCAGCCAGGTGTGCTCGACACCGAGGATCTCGGCCGCCTTGGTC 207
               |||||||||||||||| ||||||||  |||||||||||||| ||||||||||||||||  |  |
M.smeg: 32950 CCGGAGTCGACGAAACCCAGCCAGTGGTGCTCGACACCCAGGATCTCGGCCGCTTTGGCC 33009

Rv1082:    206 ATCTCGTCACGCCGGATCTCGGCGATGCGCCCATGCACGTCCGGCAGGTCCATCGCCGGG 147
               |||||||||||||  |||   |||||||||| || || || || ||||| |||||||||||||||||
M.smeg: 33010 ATCTCGTCACGGCGCACCTCGGCGATCCGGCCGTGGACCTCGGGCAGGTCCATCGCCGGA 33069

Rv1082:    146 TTGAGGATCTCGCCGCGCTCACCACCGGTCAACGTCACCACCAGCACGCGATGACCCTCG 87
               ||||| ||  || || |||||||  ||||||| |||||| ||||||  |||||  |||||||
M.smeg: 33070 TTGAGAATGTCTCCGCGCTCGCCGCCGGTCAGGGTCACCACCATGACGCGGGCACCCTCG 33129

Rv1082:    86 TCGGCGTAGCGCGCCAGGGTGGCCGCGCCCTTGCTGGACTCGTCATCGGGGTGGGCGTGC 27
              | |||||||||||||   |||  |||||||||||||||||||| ||||||||| |||
M.smeg: 33130 GCCGCGTAGCGCGCGGTGGTTGCCGCACCCTTGCTGGACTCGTCGTCCGGGTGGGCATGC 33189

Rv1082:    26 ACCGCCATCAACCGCAGTTCGCTCA 2
              ||||||||||||||||||||| ||||
M.smeg: 33190 ACCGCCATCAACCGCAGTTCACTCA 33214
```

Figure 10

SEQUENCE LISTING

<160> NUMBER OF SEQ ID NOS: 17

<210> SEQ ID NO 1
<211> LENGTH: 288
<212> TYPE: PRT
<213> ORGANISM: Mycobacterium smegmatis

<400> SEQUENCE: 1

```
Met Ser Glu Leu Arg Leu Met Ala Val His Ala His Pro Asp Asp Glu
1               5                   10                  15

Ser Ser Lys Gly Ala Ala Thr Thr Ala Arg Tyr Ala Ala Glu Gly Ala
            20                  25                  30

Arg Val Met Val Val Thr Leu Thr Gly Gly Glu Arg Gly Asp Ile Leu
        35                  40                  45

Asn Pro Ala Met Asp Leu Pro Glu Val His Gly Arg Ile Ala Glu Val
    50                  55                  60

Arg Arg Asp Glu Met Ala Lys Ala Ala Glu Ile Leu Gly Val Glu His
65                  70                  75                  80

His Trp Leu Gly Phe Val Asp Ser Gly Leu Pro Glu Gly Asp Pro Leu
                85                  90                  95

Pro Pro Leu Pro Asp Gly Cys Phe Ala Leu Val Pro Leu Glu Glu Pro
            100                 105                 110

Val Lys Arg Leu Val Arg Val Ile Arg Glu Phe Arg Pro His Val Met
        115                 120                 125

Thr Thr Tyr Asp Glu Asn Gly Gly Tyr Pro His Pro Asp His Ile Arg
130                 135                 140

Cys His Gln Val Ser Val Ala Ala Tyr Glu Ala Ala Ala Asp His Leu
145                 150                 155                 160

Leu Tyr Pro Asp Ala Gly Glu Pro Trp Ala Val Gln Lys Leu Tyr Tyr
                165                 170                 175

Asn His Gly Phe Leu Arg Gln Arg Met Gln Leu Leu Gln Glu Glu Phe
            180                 185                 190
```

```
Ala Lys Asn Gly Gln Glu Gly Pro Phe Ala Lys Trp Leu Glu His Trp
        195                 200                 205

Asp Pro Asp Asn Asp Val Phe Ala Asn Arg Val Thr Thr Arg Val His
    210                 215                 220

Cys Ala Glu Tyr Phe His Gln Arg Asp Ala Leu Arg Ala His Ala
225                 230                 235                 240

Thr Gln Ile Asp Pro Lys Gly Asp Phe Phe His Ala Pro Ile Glu Trp
                245                 250                 255

Gln Gln Arg Leu Trp Pro Thr Glu Glu Phe Glu Leu Ala Arg Ala Arg
            260                 265                 270

Val Pro Val Thr Leu Pro Glu Asp Asp Leu Phe Lys Gly Val Glu Pro
            275                 280                 285

<210> SEQ ID NO 2
<211> LENGTH: 20
<212> TYPE: PRT
<213> ORGANISM: Artificial Sequence
<220> FEATURE:
<223> OTHER INFORMATION: Acyl glucosaminyl inositol amidases N-terminal
      region with 80% homology

<400> SEQUENCE: 2

Met Ser Glu Leu Arg Leu Met Ala Val His Ala His Pro Asp Asp Glu
1               5                   10                  15

Ser Ser Lys Gly
            20

<210> SEQ ID NO 3
<211> LENGTH: 7
<212> TYPE: PRT
<213> ORGANISM: Artificial Sequence
<220> FEATURE:
<223> OTHER INFORMATION: Domain 1 of an amide hydrolase
<220> FEATURE:
<221> NAME/KEY: MISC_FEATURE
<222> LOCATION: (1)..(1)
<223> OTHER INFORMATION: Xaa is either Val or Phe

<400> SEQUENCE: 3

Xaa His Ala His Pro Asp Asp
1               5

<210> SEQ ID NO 4
<211> LENGTH: 5
<212> TYPE: PRT
<213> ORGANISM: Artificial Sequence
<220> FEATURE:
<223> OTHER INFORMATION: Domain 3 of an amide hydrolase
<220> FEATURE:
<221> NAME/KEY: MISC_FEATURE
<222> LOCATION: (1)..(1)
<223> OTHER INFORMATION: Xaa is either Asp or His
<220> FEATURE:
<221> NAME/KEY: MISC_FEATURE
<222> LOCATION: (5)..(5)
<223> OTHER INFORMATION: Xaa is either Ile or Val

<400> SEQUENCE: 4

Xaa Pro Asp His Xaa
1               5

<210> SEQ ID NO 5
<211> LENGTH: 8
<212> TYPE: PRT
<213> ORGANISM: Artificial Sequence
```

```
<220> FEATURE:
<223> OTHER INFORMATION: Domain 4 of an amide hydrolase
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is either Ala or Ser
<220> FEATURE:
<221> NAME/KEY: MISC_FEATURE
<222> LOCATION: (6)..(6)
<223> OTHER INFORMATION: Xaa is either Ala or Val
<220> FEATURE:
<221> NAME/KEY: MISC_FEATURE
<222> LOCATION: (7)..(7)
<223> OTHER INFORMATION: Xaa is either Thr or Ser

<400> SEQUENCE: 5

Ala Leu Xaa Xaa His Xaa Xaa Gln
1               5

<210> SEQ ID NO 6
<211> LENGTH: 862
<212> TYPE: DNA
<213> ORGANISM: Mycobacterium smegmatis

<400> SEQUENCE: 6
ggctcgaccc ccttgaacag gtcgtcctcg ggcagcgtga ccggcacgcg ggcccgcgcg       60
agctcgaact cctcggtcgg ccacaaccgc tgctgccact cgatcgggc gtggaagaag       120 tcgcccttgg gatcgatctg tgtcgcgtgc gcacgcaacg cgtcgtcacg ctggtggaag      180
tactccgcgc agtgcacgcg ggtggtcacc cggttggcga acacgtcgtt gtcgggatcc      240
cagtgctcga gccatttggc gaacgggccc tcctgcccgt tcttggcgaa ctcctcctgc      300
aggagctgca tgcgctgacg gaggaagcca tggttgtagt acagcttctg caccgcccac      360
ggctcaccgg cgtcgggata cagcaggtgg tcggccgcgg cctcgtacgc ggccaccgac      420
acctggtggc agcggatgtg gtcgggatgc gggtaaccac cgttctcgtc gtatgtggtc      480
atcacgtgcg ggcggaactc gcggatcacc cgcaccagac gcttgacggg ctcctcgagc      540
gggaccaggg cgaaacaccc gtcgggcagc ggcggcagcg ggtcaccctc ggcaatccg      600 gagtcgacga aacccagcca gtggtgctcg acacccagga tctcggccgc tttggccatc      660
tcgtcacggc gcacctcggc gatccggccg tggacctcgg gcaggtccat cgccggattg      720
agaatgtctc cgcgctcgcc gccggtcagg gtcaccacca tgacgcgggc accctcggcc      780
gcgtagcgcg cggtggttgc cgcacccttg ctggactcgt cgtccgggtg ggcatgcacc      840
gccatcaacc gcagttcact ca                                               862

<210> SEQ ID NO 7
<211> LENGTH: 288
<212> TYPE: PRT
<213> ORGANISM: Mycobacterium tuberculosis

<400> SEQUENCE: 7

Met Ser Glu Leu Arg Leu Met Ala Val His Ala His Pro Asp Asp Glu
1               5                   10                  15

Ser Ser Lys Gly Ala Ala Thr Leu Ala Arg Tyr Ala Asp Glu Gly His
                20                  25                  30

Arg Val Leu Val Val Thr Leu Thr Gly Gly Glu Arg Gly Glu Ile Leu
            35                  40                  45
```

```
Asn Pro Ala Met Asp Leu Pro Asp Val His Gly Arg Ile Ala Glu Ile
 50                  55                  60

Arg Arg Asp Glu Met Thr Lys Ala Ala Glu Ile Leu Gly Val Glu His
 65                  70                  75                  80

Thr Trp Leu Gly Phe Val Asp Ser Gly Leu Pro Lys Gly Asp Leu Pro
                 85                  90                  95

Pro Pro Leu Pro Asp Asp Cys Phe Ala Arg Val Pro Leu Glu Val Ser
                100                 105                 110

Thr Glu Ala Leu Val Arg Val Arg Glu Phe Arg Pro His Val Met
            115                 120                 125

Thr Thr Tyr Asp Glu Asn Gly Gly Tyr Pro His Pro Asp His Ile Arg
        130                 135                 140

Cys His Gln Val Ser Val Ala Ala Tyr Glu Ala Gly Asp Phe Cys
145                 150                 155                 160

Arg Phe Pro Asp Ala Gly Glu Pro Trp Thr Val Ser Lys Leu Tyr Tyr
                165                 170                 175

Val His Gly Phe Leu Arg Glu Arg Met Gln Met Leu Gln Asp Glu Phe
                180                 185                 190

Ala Arg His Gly Gln Arg Gly Pro Phe Glu Gln Trp Leu Ala Tyr Trp
            195                 200                 205

Asp Pro Asp His Asp Phe Leu Thr Ser Arg Val Thr Thr Arg Val Glu
210                 215                 220

Cys Ser Lys Tyr Phe Ser Gln Arg Asp Ala Leu Arg Ala His Ala
225                 230                 235                 240

Thr Gln Ile Asp Pro Asn Ala Glu Phe Phe Ala Ala Pro Leu Ala Trp
                245                 250                 255

Gln Glu Arg Leu Trp Pro Thr Glu Glu Phe Leu Ala Arg Ser Arg
            260                 265                 270

Ile Pro Ala Arg Pro Pro Glu Thr Glu Leu Phe Ala Gly Ile Glu Pro
                275                 280                 285

<210> SEQ ID NO 8
<211> LENGTH: 225
<212> TYPE: PRT
<213> ORGANISM: Artificial Sequence
<220> FEATURE:
<223> OTHER INFORMATION: Consensus sequence between Mycobacterium
      tuberculosis and Mycobacterium smegmatis

<400> SEQUENCE: 8

Met Ser Glu Leu Arg Leu Met Ala Val His Ala His Pro Asp Asp Glu
  1               5                  10                  15

Ser Ser Lys Gly Ala Ala Thr Ala Arg Tyr Ala Glu Gly Arg Val Val
             20                  25                  30

Val Thr Leu Thr Gly Gly Glu Arg Gly Ile Leu Asn Pro Ala Met Asp
         35                  40                  45

Leu Pro Val His Gly Arg Ile Ala Glu Arg Arg Asp Glu Met Lys Ala
     50                  55                  60

Ala Glu Ile Leu Gly Val Glu His Trp Leu Gly Phe Val Asp Ser Gly
 65                  70                  75                  80

Leu Pro Gly Asp Pro Pro Leu Pro Asp Cys Phe Ala Val Pro Leu Glu
                 85                  90                  95

Leu Val Arg Val Arg Glu Phe Arg Pro His Val Met Thr Thr Tyr Asp
                100                 105                 110

Glu Asn Gly Gly Tyr Pro His Pro Asp His Ile Arg Cys His Gln Val
            115                 120                 125
```

```
Ser Val Ala Ala Tyr Glu Ala Ala Asp Pro Asp Ala Gly Glu Pro Trp
    130                 135                 140
Val Lys Leu Tyr Tyr His Gly Phe Leu Arg Arg Met Gln Leu Gln Glu
145                 150                 155                 160
Phe Ala Gly Gln Gly Pro Phe Trp Leu Trp Asp Pro Asp Asp Arg Val
                165                 170                 175
Thr Thr Arg Val Cys Tyr Phe Gln Arg Asp Asp Ala Leu Arg Ala His
            180                 185                 190
Ala Thr Gln Ile Asp Pro Phe Phe Ala Pro Trp Gln Arg Leu Trp Pro
        195                 200                 205
Thr Glu Glu Phe Glu Leu Ala Arg Arg Pro Pro Glu Leu Phe Gly Glu
    210                 215                 220
Pro
225

<210> SEQ ID NO 9
<211> LENGTH: 862
<212> TYPE: DNA
<213> ORGANISM: Mycobacterium tuberculosis

<400> SEQUENCE: 9
ggctcgatcc cggcgaacaa ttcggtctcc ggtgggcgcg cggggatacg cgagcgagcc      60
aactcgaatt cctcggtcgg ccacagccgc tcctgccagg caagcggggc ggcgaagaat     120
tcggcgttcg ggtcgatctg ggtggcatgc gcgcgcaacg catcgtcgcg ttggctgaag     180
tatttcgagc actcgacccg ggtggtcact cggctggtga aaagtcatg gtcggggtcc      240 cagtacgcca gccattgttc gaatgggccg cgttggccgt gccgggcgaa ctcatcctgc     300
aacatctgca tccgctcccg caggaagccg tggacgtagt acagcttgga caccgtccac     360
ggctcacccg cgtcgggaaa ccggcaaaag tcaccggccg cctcgtaggc agccaccgaa     420
acctgatgga agcgaatgtg gtcgggatgt gggtagccgc cgttctcgtc gtaggtggtc     480
atcacgtgcg gccgaaactc gcgaaccacc cgcaccagcg cctcggtgga cacctccagc     540
ggtacccgcg cgaagcagtc atcaggcagc ggtggcggta aatcacccct aggtagcccg     600
gagtcgacga agcccagcca ggtgtgctcg acaccgagga tctcggccgc cttggtcatc     660
tcgtcacgcc ggatctcggc gatgcgccca tgcacgtccg gcaggtccat cgccgggttg     720
aggatctcgc gcgctcacc accggtcaac gtcaccacca gcacgcgatg accctcgtcg     780
gcgtagcgcg ccagggtggc cgcgcccttg ctggactcgt catcggggtg ggcgtgcacc     840
gccatcaacc gcagttcgct ca                                             862

<210> SEQ ID NO 10
<211> LENGTH: 29
<212> TYPE: DNA
<213> ORGANISM: Artificial Sequence
<220> FEATURE:
<223> OTHER INFORMATION: Amplification primer for RV 1082

<400> SEQUENCE: 10
tagccatggt gagcgaactg cggttgatg                                       29

<210> SEQ ID NO 11
<211> LENGTH: 28
<212> TYPE: DNA
<213> ORGANISM: Artificial Sequence
<220> FEATURE:
<223> OTHER INFORMATION: Amplification primer for RV 1082
```

-continued

```
<400> SEQUENCE: 11
ggatcccgat cccggcgaac aattcggt                                        28

<210> SEQ ID NO 12
<211> LENGTH: 24
<212> TYPE: PRT
<213> ORGANISM: Artificial Sequence
<220> FEATURE:
<223> OTHER INFORMATION: Combinatorial library
<220> FEATURE:
<221> NAME/KEY: MISC_FEATURE
<222> LOCATION: (1)..(1)
<223> OTHER INFORMATION: Xaa is either Ser, Thr, Asn, or Gln
<220> FEATURE:
<221> NAME/KEY: MISC_FEATURE
<222> LOCATION: (2)..(2)
<223> OTHER INFORMATION: Xaa is either Gly, Ala, Val, Leu, or Ile
<220> FEATURE:
<221> NAME/KEY: MISC_FEATURE
<222> LOCATION: (3)..(3)
<223> OTHER INFORMATION: Xaa is either Arg, Lys or His
<220> FEATURE:
<221> NAME/KEY: MISC_FEATURE
<222> LOCATION: (4)..(4)
<223> OTHER INFORMATION: Xaa is either Gly, Ala, Val, Leu, Ile, Asp, or
      Glu
<220> FEATURE:
<221> NAME/KEY: MISC_FEATURE
<222> LOCATION: (5)..(5)
<223> OTHER INFORMATION: Xaa is either Gly, Ala, Val, Leu, Ile, Asn, or
      Gln
<220> FEATURE:
<221> NAME/KEY: MISC_FEATURE
<222> LOCATION: (6)..(6)
<223> OTHER INFORMATION: Xaa is either Arg, Lys, His, Tyr, or Phe
<220> FEATURE:
<221> NAME/KEY: MISC_FEATURE
<222> LOCATION: (7)..(7)
<223> OTHER INFORMATION: Xaa is either Asp or Glu
<220> FEATURE:
<221> NAME/KEY: MISC_FEATURE
<222> LOCATION: (8)..(8)
<223> OTHER INFORMATION: Xaa is either Pro, Gly, Ser, or Thr
<220> FEATURE:
<221> NAME/KEY: MISC_FEATURE
<222> LOCATION: (9)..(9)
<223> OTHER INFORMATION: Xaa is either Gly, Ala, Val, Leu, Ile, Asp or
      Glu
<220> FEATURE:
<221> NAME/KEY: MISC_FEATURE
<222> LOCATION: (10)..(10)
<223> OTHER INFORMATION: Xaa is either Gly, Ala, Val, Leu, Ile, or an
      amino acid gap
<220> FEATURE:
<221> NAME/KEY: MISC_FEATURE
<222> LOCATION: (11)..(11)
<223> OTHER INFORMATION: Xaa is either Gly, Ala, Val, Leu, Ile, Ser, or
      Thr
<220> FEATURE:
<221> NAME/KEY: MISC_FEATURE
<222> LOCATION: (12)..(12)
<223> OTHER INFORMATION: Xaa is either Phe, Tyr, Trp, or an amino acid
      gap
<220> FEATURE:
<221> NAME/KEY: MISC_FEATURE
<222> LOCATION: (13)..(13)
<223> OTHER INFORMATION: Xaa is either Ser or Thr
<220> FEATURE:
<221> NAME/KEY: MISC_FEATURE
<222> LOCATION: (14)..(14)
<223> OTHER INFORMATION: Xaa is either Gly, Ala, Val, Leu, Ile, Arg,
      Lys, or His
<220> FEATURE:
<221> NAME/KEY: MISC_FEATURE
<222> LOCATION: (15)..(15)
<223> OTHER INFORMATION: Xaa is either Gly, Ala, Val, Leu, Ile, Ser, or
      Thr
```

```
<220> FEATURE:
<221> NAME/KEY: MISC_FEATURE
<222> LOCATION: (16)..(16)
<223> OTHER INFORMATION: Xaa is either Gly, Ala, Val, Leu, or Ile
<220> FEATURE:
<221> NAME/KEY: MISC_FEATURE
<222> LOCATION: (17)..(17)
<223> OTHER INFORMATION: Xaa is either Glx
<220> FEATURE:
<221> NAME/KEY: MISC_FEATURE
<222> LOCATION: (18)..(18)
<223> OTHER INFORMATION: Xaa is either Gly, Ala, Val, Leu, Ile, Lys,
    His, or Arg
<220> FEATURE:
<221> NAME/KEY: MISC_FEATURE
<222> LOCATION: (19)..(19)
<223> OTHER INFORMATION: Xaa is either Arg or Gln
<220> FEATURE:
<221> NAME/KEY: MISC_FEATURE
<222> LOCATION: (20)..(20)
<223> OTHER INFORMATION: Xaa is either Gly, Ala, Val, Leu or Ile
<220> FEATURE:
<221> NAME/KEY: MISC_FEATURE
<222> LOCATION: (21)..(21)
<223> OTHER INFORMATION: Xaa is either Gly, Ala, Val, Leu, or Ile
<220> FEATURE:
<221> NAME/KEY: MISC_FEATURE
<222> LOCATION: (22)..(22)
<223> OTHER INFORMATION: Xaa is either Gly, Ala, Val, Leu, Ile, Lys,
    His, or Arg
<220> FEATURE:
<221> NAME/KEY: MISC_FEATURE
<222> LOCATION: (23)..(23)
<223> OTHER INFORMATION: Xaa is either Gly, Ala, Val, Leu, Ile, Thr, or
    Ser
<220> FEATURE:
<221> NAME/KEY: MISC_FEATURE
<222> LOCATION: (24)..(24)
<223> OTHER INFORMATION: Xaa is either Gly, Ala, Val, Leu, Ile, Ser, Thr
    or an amino acid gap

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 13
<211> LENGTH: 270
<212> TYPE: PRT
<213> ORGANISM: Streptomyces lincolnensis

<400> SEQUENCE: 13

Met Thr Gln Cys Leu Leu Thr Val His Ala His Pro Asp Asp Glu Ala
1               5                   10                  15

Ser Arg Gly Gly Ala Thr Val Ala His Tyr Thr Ala Gln Gly Val Arg
            20                  25                  30

Ala Val Leu Val Thr Cys Thr Asp Gly Gly Ala Gly Glu Val Leu Asn
        35                  40                  45

Pro Ala Val Thr Asp Asp Phe Thr Pro Glu Arg Phe Val Ala Val Arg
    50                  55                  60

Ser Ala Glu Leu Asp Ala Ser Ala Arg Asn Leu Gly Tyr Ser Ala Val
65                  70                  75                  80

His Arg Leu Gly Tyr Arg Asp Ser Gly Met Asp Gly Thr Ala Gly Gly
                85                  90                  95

Ala Glu Ala Phe Val Arg Ala Pro Leu Asp Glu Ala Ala Thr Arg Leu
            100                 105                 110
```

```
Ala Arg Val Ile Ala Asp Glu Arg Pro Asp Val Val Ile Gly Tyr Gly
        115                 120                 125

Thr Asn His Thr Arg Asp Pro His Pro Asp His Ile Arg Ala Asn Glu
    130                 135                 140

Val Leu Thr Arg Arg Val Asp Leu Leu Asp His Thr Pro Ala Val Tyr
145                 150                 155                 160

His Ile Ala Phe Ser Arg Arg His Arg Ala Leu His Gln Ala Cys
                165                 170                 175

Val Asp Ser Gly Val Pro Ser Pro Tyr Glu Gly Gly Leu Ser Ala Pro
                180                 185                 190

Pro Gly Ala Phe Asp Asp Glu Trp Ile Thr Thr Leu Val Asp Val Thr
        195                 200                 205

Lys Gly Asp Ala Val Glu Arg Arg Leu Asp Ala Leu Arg Ser His Val
        210                 215                 220

Thr Gln Val Pro Pro Ala Ser Gly Trp Phe Ala Leu Ser Pro Gln Gln
225                 230                 235                 240

Leu Arg Asp Ala Phe Pro Tyr Glu Glu Tyr Thr Arg Val Gly Ala Ala
                245                 250                 255

Pro Arg Glu Ala Val Val His Asp Leu Phe Thr Ala Pro Ala
        260                 265                 270

<210> SEQ ID NO 14
<211> LENGTH: 255
<212> TYPE: PRT
<213> ORGANISM: Amycolatopsis mediterranei

<400> SEQUENCE: 14

Met Gly Thr Leu Val Ser Phe His Ala His Pro Asn Asp Asp Thr Thr
1               5                   10                  15

Thr Cys Gly Gly Val Leu Arg Lys Ala His Glu Asp Gly His Arg Val
                20                  25                  30

Val Leu Val Leu Ala Thr Arg Gly Glu Leu Gly Tyr Asn Pro Asp Gly
            35                  40                  45

Leu Leu Ala Glu Gly Glu Thr Leu Gly Asp Arg Arg Ala Val Glu Ala
    50                  55                  60

Arg Ala Ala Asp Val Leu Gly Val Asp Arg Leu Glu Phe Leu Gly
65                  70                  75                  80

Tyr Thr Asp Ser Gly Met Thr Ala Ala Asp Gly Ala Gly Thr Phe
                85                  90                  95

Gln Thr Ala Asp Val Glu Glu Ala Arg Lys Leu Ala Ala Ile Leu
        100                 105                 110

Arg Glu Glu Arg Ala Asp Val Leu Thr Val Tyr Asp Glu Lys Gly Thr
        115                 120                 125

Tyr Gly Asp Pro Asp His Ile Gln Val His Arg Val Gly Thr Arg Ala
130                 135                 140

Ala Glu Leu Ala Gly Thr Ala Lys Val Phe Gln Ser Thr Ile Asn Arg
145                 150                 155                 160

Glu His Ile Lys Ala Asn Gln Arg Val Leu Ala Glu Gln Ala Gly Val
                165                 170                 175

Asp Leu Pro Ala Gly Pro Asp Phe Gly Thr Pro Glu Ala Glu Leu Thr
            180                 185                 190

Cys Arg Val Asp Val Ser Ala Tyr Thr Glu Tyr Lys Arg Lys Ala Leu
        195                 200                 205

Leu Ala His Ala Ser Gln Ile Thr Pro Gln Ser Thr Leu Phe Thr Asp
    210                 215                 220
```

-continued

```
Leu Pro Glu Asp Thr Phe Arg Thr Met Phe Gly Thr Glu Trp Phe Ile
225                 230                 235                 240

Arg Ala Gly Gln Gly Pro Gly Ile Thr Glu Thr Asp Leu Met Ala
                245                 250                 255

<210> SEQ ID NO 15
<211> LENGTH: 303
<212> TYPE: PRT
<213> ORGANISM: Mycobacterium tuberculosis

<400> SEQUENCE: 15

Met Ser Glu Thr Pro Arg Leu Leu Phe Val His Ala His Pro Asp Asp
1               5                   10                  15

Glu Ser Leu Ser Asn Gly Ala Thr Ile Ala His Tyr Thr Ser Arg Gly
            20                  25                  30

Ala Gln Val His Val Val Thr Cys Thr Leu Gly Glu Glu Gly Glu Val
        35                  40                  45

Ile Gly Asp Arg Trp Ala Gln Leu Thr Ala Asp His Ala Asp Gln Leu
    50                  55                  60

Gly Gly Tyr Arg Ile Gly Glu Leu Thr Ala Ala Leu Arg Ala Leu Gly
65                  70                  75                  80

Val Ser Ala Pro Ile Tyr Leu Gly Gly Ala Gly Arg Trp Arg Asp Ser
                85                  90                  95

Gly Met Ala Gly Thr Asp Gln Arg Ser Gln Arg Arg Phe Val Asp Ala
            100                 105                 110

Asp Pro Arg Gln Thr Val Gly Ala Leu Val Ala Ile Ile Arg Glu Leu
        115                 120                 125

Arg Pro His Val Val Thr Tyr Asp Pro Asn Gly Gly Tyr Gly His
    130                 135                 140

Pro Asp His Val His Thr His Thr Val Thr Thr Ala Ala Val Ala Ala
145                 150                 155                 160

Ala Gly Val Gly Ser Gly Thr Ala Asp His Pro Gly Asp Pro Trp Thr
                165                 170                 175

Val Pro Lys Phe Tyr Trp Thr Val Leu Gly Leu Ser Ala Leu Ile Ser
            180                 185                 190

Gly Ala Arg Ala Leu Val Pro Asp Asp Leu Arg Pro Glu Trp Val Leu
        195                 200                 205

Pro Arg Ala Asp Glu Ile Ala Phe Gly Tyr Ser Asp Asp Gly Ile Asp
    210                 215                 220

Ala Val Val Glu Ala Asp Glu Gln Ala Arg Ala Ala Lys Val Ala Ala
225                 230                 235                 240

Leu Ala Ala His Ala Thr Gln Val Val Gly Pro Thr Gly Arg Ala
                245                 250                 255

Ala Ala Leu Ser Asn Asn Leu Ala Leu Pro Ile Leu Ala Asp Glu His
            260                 265                 270

Tyr Val Leu Ala Gly Gly Ser Ala Gly Ala Arg Asp Glu Arg Gly Trp
        275                 280                 285

Glu Thr Asp Leu Leu Ala Gly Leu Gly Phe Thr Ala Ser Gly Thr
    290                 295                 300

<210> SEQ ID NO 16
<211> LENGTH: 288
<212> TYPE: PRT
<213> ORGANISM: Mycobacterium tuberculosis
```

-continued

```
<400> SEQUENCE: 16

Val Ser Glu Leu Arg Leu Met Ala Val His Ala His Pro Asp Asp Glu
1               5                   10                  15

Ser Ser Lys Gly Ala Ala Thr Leu Ala Arg Tyr Ala Asp Glu Gly His
            20                  25                  30

Arg Val Leu Val Val Thr Leu Thr Gly Gly Glu Arg Gly Glu Ile Leu
        35                  40                  45

Asn Pro Ala Met Asp Leu Pro Asp Val His Gly Arg Ile Ala Glu Ile
    50                  55                  60

Arg Arg Asp Glu Met Thr Lys Ala Ala Glu Ile Leu Gly Val Glu His
65                  70                  75                  80

Thr Trp Leu Gly Phe Val Asp Ser Gly Leu Pro Lys Gly Asp Leu Pro
                85                  90                  95

Pro Pro Leu Pro Asp Asp Cys Phe Ala Arg Val Pro Leu Glu Val Ser
            100                 105                 110

Thr Glu Ala Leu Val Arg Val Val Arg Glu Phe Arg Pro His Val Met
        115                 120                 125

Thr Thr Tyr Asp Glu Asn Gly Gly Tyr Pro His Pro Asp His Ile Arg
    130                 135                 140

Cys His Gln Val Ser Val Ala Ala Tyr Glu Ala Ala Gly Asp Phe Cys
145                 150                 155                 160

Arg Phe Pro Asp Ala Gly Glu Pro Trp Thr Val Ser Lys Leu Tyr Tyr
                165                 170                 175

Val His Gly Phe Leu Arg Glu Arg Met Gln Met Leu Gln Asp Glu Phe
            180                 185                 190

Ala Arg His Gly Gln Arg Gly Pro Phe Glu Gln Trp Leu Ala Tyr Trp
        195                 200                 205

Asp Pro Asp His Asp Phe Leu Thr Ser Arg Val Thr Thr Arg Val Glu
    210                 215                 220

Cys Ser Lys Tyr Phe Ser Gln Arg Asp Asp Ala Leu Arg Ala His Ala
225                 230                 235                 240

Thr Gln Ile Asp Pro Asn Ala Glu Phe Phe Ala Ala Pro Leu Ala Trp
                245                 250                 255

Gln Glu Arg Leu Trp Pro Thr Glu Glu Phe Glu Leu Ala Arg Ser Arg
            260                 265                 270

Ile Pro Ala Arg Pro Pro Glu Thr Glu Leu Phe Ala Gly Ile Glu Pro
        275                 280                 285

<210> SEQ ID NO 17
<211> LENGTH: 290
<212> TYPE: PRT
<213> ORGANISM: Mycobacterium leprae

<400> SEQUENCE: 17

Met Ser Glu Leu Arg Leu Met Ala Val His Ala His Pro Asp Asp Glu
1               5                   10                  15

Ser Ser Lys Gly Ala Ala Thr Leu Ala Arg Tyr Ala Asp Glu Gly His
            20                  25                  30

Arg Val Leu Val Val Thr Leu Thr Gly Gly Glu Arg Gly Glu Ile Leu
        35                  40                  45

Asn Pro Ala Met Asp Leu Pro Asp Val His Gly His Ile Ala Glu Ile
    50                  55                  60

Arg Arg Asp Glu Met Ala Lys Ala Ala Glu Ile Leu Gly Val Glu His
65                  70                  75                  80
```

```
Thr Trp Leu Gly Phe Ile Asp Ser Gly Leu Pro Lys Gly Asp Pro Pro
            85                  90                  95

Pro Pro Leu Pro Asp Asp Cys Phe Ala Leu Val Pro Leu Glu Val Cys
            100                 105                 110

Thr Glu Ala Leu Val Arg Val Val Arg Lys Phe Arg Pro His Val Leu
            115                 120                 125

Thr Thr Tyr Asp Glu Asn Gly Gly Tyr Pro His Pro Asp His Ile Arg
            130                 135                 140

Cys His Gln Val Ser Val Asp Ala Tyr Glu Ala Ala Cys Asp Tyr Arg
145                 150                 155                 160

Arg Phe Pro Asp Ala Gly Lys Pro Trp Thr Val Ser Lys Leu Tyr Tyr
            165                 170                 175

Asn His Gly Phe Leu Arg Ala Arg Met Gln Leu Leu His Asp Glu Phe
            180                 185                 190

Ala Lys His Gly Gln Ala Gly Pro Phe Asp Lys Trp Leu Ala Gln Ser
            195                 200                 205

Asn Pro Ala His Asp Pro Phe Glu Ser Arg Val Thr Thr Arg Val Glu
            210                 215                 220

Cys Ser Ala Tyr Phe Ser Gln Arg Asp Asp Ala Leu Arg Ala His Ala
225                 230                 235                 240

Thr Gln Ile Asp Pro Lys Ala Glu Phe Phe Ala Ala Pro Ile Ser Trp
            245                 250                 255

Gln Gln Arg Leu Trp Pro Thr Glu Glu Phe Glu Leu Ala Arg Ser Arg
            260                 265                 270

Val Pro Thr Arg Leu Pro Glu His Asp Leu Phe Ala Gly Ile Glu Ala
            275                 280                 285

Ala Gly
    290
```

BACTERIAL MYCOTHIOL S-CONJUGATE AMIDASE FAMILY

RELATED APPLICATION

This application is a divisional application of U.S. application Ser. No. 09/733,569 filed Dec. 7, 2000, now abandoned which claims priority under 35 USC § 119(e) of U.S. Application Ser. No. 60/169,503 filed Dec. 7, 1999, now abandoned. The disclosure of each of the prior applications is considered part of and is incorporated by reference in the disclosure of this application.

FIELD OF THE INVENTION

The present invention generally relates to a family of enzymatic compounds produced by bacteria and methods of their use in drug discovery and degradation of toxic substances, and more specifically to acyl glucosaminyl inositol amidases and methods of their use.

BACKGROUND OF THE INVENTION

Aerobic organisms are subjected to oxidative stress from many sources, including atmospheric oxygen, basal metabolic activities, and, in the case of pathogenic microorganisms, toxic oxidants from the host phagocytic response intended to destroy the bacterial invader. Glutathione (GSH) is the dominant low molecular weight thiol in most eukaryotes and Gram-negative bacteria, and it plays a key role in protection of the cell against oxygen toxicity and electrophilic toxins (R. C. Fahey and A. R. Sundquist (1991) *Adv. Enzymol.* 64:1–53; Dolphin, et al, (1989) *Glutathione: Chemical, Biochemical, and Medical Aspects* pp 45–84, John Wiley & Sons, New York). However, actinomycetes, including *Streptomyces* and *Mycobacteria* do not make GSH but produce millimolar levels of mycothiol (MSH, AcCys-GlcN-Ins), an unusual conjugate of N-acetylcysteine (AcCys) with 1-D-myo-inosityl-2-amino-2-deoxy-α-D-glucopyranoside (GlcN-Ins) (G. L. Newton, et al. (1996) *J. Bacteriol.* 178:1990–1995; S. Sakuda, et al., (1994) Biosci. Biotech. Biochem. 58:1347–1348; H. S. C. Spies and D. J. Steenkamp, (1994) *Eur. J. Biochem.* 224:203–213; G. L. Newton, et al. (1995) *Eur. J. Biochem.* 230:821–825) (FIG. 1A).

Mycothiol autoxidizes more slowly than glutathione (G. L. Newton, et al. (1995) *Eur. J. Biochem.* 230:821–825) and mutants of *Mycobacterium smegmatis* defective in the biosynthesis of mycothiol have increased sensitivity to hydrogen peroxide and antibiotics relative to the parent strain (G. L. Newton, et al. (1999) *Biochem. Biophys. Res. Commun.* 255:239–244). This observation suggests that mycothiol may play a key role in the protection of actinomycetes against oxygen toxicity and reactive toxins. The biochemistry of mycothiol appears to have evolved completely independently of that of glutathione.

However, it has already been established that the metabolism of mycothiol parallels that of glutathione metabolism in two enzymatic processes. First, formaldehyde is detoxified in glutathione-producing organisms by NAD/glutathione-dependent formaldehyde dehydrogenase (L. Uotila, et al. (1989) in *Glutathione: Chemical, Biochemical, and Medical Aspects—Part A* (D. Dolphin, et al., Eds.) pp 517–551, John Wiley & Sons, et al.). An analogous process involving NAD/mycothiol-dependent formaldehyde dehydrogenase has been identified in the actinomycete *Amycolatopsis methanolica* (M. Misset-Smits, et al. (1997) FEBS Lett. 409:221–222). This enzyme has been sequenced (A. Norin, et al. (1997) *Eur. J. Biochem.* 248:282–289).

A mycothiol homolog of glutathione reductase was recently cloned from *M tuberculosis* and expressed in *M. smegmatis* (M. P. Patel, et al. (1999) *J. Amer. Chem. Soc.* 120:11538–11539, M. P. Patel, et al. (1999) *Biochem.* 38:11827–11833). The reductase is reasonably specific for the disulfide of mycothiol but is also active with the disulfide of AcCys-GlcN, the desmyo-inositol derivative of mycothiol (M. P. Patel, et al. (1999) supra.). Therefore, there is a need in the art for investigation of the details of the metabolism of mycothiol and comparison with the established roles for the metabolism of glutathione.

Antibiotic resistance of pathogenic bacteria, including pathogenic actinomycetes, such as *M. tuberculosis*, is a well-known problem faced by medical practitioners in treatment of bacterial diseases. Therefore, there is a further need in the art for screening techniques to discover new antibiotics and drugs effective to reduce resistance to existing antibiotics in treatment of bacterial infections in humans and in other mammals, such as domestic and farm animals.

Air, soil and groundwater in areas surrounding industrial centers and farming areas are becoming increasingly polluted with simple organic compounds with have long lifetimes in the environment. These compounds include, but are not limited to 1, 2 dibromoethane, 1,2 dichloroethane, perchloroethene, trichloroethene, isoprene, and vinyl chloride. They are from pesticides, industrial degreasers, solvents, and from the production polyvinyl chloride polymers (plastics). Organisms have recently been isolated from contaminated environments that have the ability to detoxify, and in some cases grow using these pollutants as a sole carbon source. There is great interest in industrialized countries in using microorganisms for biodegradation of these pollutants in soil and groundwater, a field generally known as bioremediation.

Recent reports indicate that vinyl chloride, 1,2 dibromoethane, and numerous other haloalkanes are detoxified by mycobacteria (A. Jesenke et al., *Microbiology*, 66:2219–222 (2000); S. Hartmans, and A. M. DeBont, *Applied and Environmental Microbiology*, 58:1220–1226 (1992).; G. J. Poelarends, et al. *J. Bacteriol*, 181:2050–2058, (1999)). These toxic compounds are generally dehalogenated to form epoxides or monohaloaldehydes that are in turn toxic compounds to microorganisms until they are conjugated with thiols. Many of these organisms are actinomycetes and are likely to have mycothiol and mycothiol biosynthesis (G. L. Newton, et al. (1996) *J. Bacteriol.*, 178:1990–1995). In the case of mycobacteria, mycothiol is the major low molecular weight thiol and will form a mycothiol conjugate. The product of this conjugation may still be toxic. Although such studies have shown the need for low molecular weight thiols in the detoxification reactions for toxins and have assayed their organisms for glutathione, to date such studies have not acknowledged the occurrence of mycothiol in mycobacteria.

Another actinomycete, *Rhodococcus* sp. Strain AD45 has been extensively studied for detoxification of isoprene, 1,2 dibromoethane and 1,2 dichloroethene (J. E. T. van Hylckama Vlieg, et al., *Current Opinion in Microbiology*, 3:257–262 (2000)). The enzymes responsible for the detoxification of these toxic substances were claimed to include a glutathione S-transferase and a glutathione conjugate specific dehydrogenase (J. E. T. van Hylckama Vlieg, et al, *Applied and Environmental Microbiology*, 64:2800–2805 (1998); J. E. T. van Hylckama Vlieg, et al. *J. Bacteriology*, 181:2094–2101 (1999); J. E. T. Van Hylckama Vlieg et al., J. Bacteriology 182:1956–1963 (2000).

Thus, there is a further need in the art for methods and compounds useful for detoxification of environmental toxins.

SUMMARY OF THE INVENTION

The present invention overcomes these and other problems in the art by providing a family of purified acyl glucosaminyl inositol amidase polypeptides with enzymatic amidase activity for glucosaminyl inositol (GlcN-Ins)-containing substrates. The invention acyl glucosaminyl inositol amidases are characterized by comprising an N-terminal region with an amino acid sequence with at least 80% sequence identity to SEQ ID NO: 2, having four highly conserved domains wherein three of the domains contain conserved histidine residues, and having amidase activity against glucosaminyl inositol-containing amides.

In another embodiment according to the present invention, there are provided methods for identifying an inhibitor of acyl glucosaminyl inositol amidase activity by contacting a candidate inhibitor with an acyl glucosaminyl inositol amidase or a polynucleotide encoding the amidase in the presence of an GlcN-Ins-containing amide under suitable conditions and then determining the presence or absence of breakdown products of the amide indicative of amide hydrolase activity. The substantial absence of the amide hydrolase activity indicates the candidate compound is an inhibitor of acyl glucosaminyl inositol amidase activity.

In still another embodiment according to the present invention, there are provided methods for increasing production of antibiotic by antibiotic-producing bacteria by contacting the antibiotic-producing bacteria with a compound that increases intracellular production by the bacteria in culture of an acyl glucosaminyl inositol amidase. The increase in production of the amidase increases the production of antibiotic by the bacteria by increasing resistance of the bacteria to the antibiotic.

In yet another embodiment according to the present invention, there are provided methods for decreasing the antibiotic-resistance of pathogenic acyl glucosaminyl inositol amidase-producing bacteria by introducing into the bacteria an inhibitor of acyl glucosaminyl inositol amidase activity. The intracellular presence of the inhibitor decreases activity of the amidase, thereby decreasing the antibiotic-resistance of the bacteria as compared with untreated control bacteria.

In yet another embodiment according to the present invention, there are provided methods for detoxifying a toxic substance comprising contacting the toxic substance with bacteria transformed with a polynucleotide that encodes an acyl glucosaminyl inositol amidase and expressing the amidase in order to detoxify the toxic substance.

In still another embodiment according to the present invention, there are provided processes for preparation of GlcN-Ins by contacting an N-acyl glucosaminyl inositol under suitable conditions with an acyl glucosaminyl inositol amidase so as to therein obtain the GlcN-Ins.

BRIEF DESCRIPTION OF THE FIGURES

FIG. 1A is a drawing showing the chemical structure of mycothiol (AcCys-GlcN-Ins) (MSH), chemical name 1-D-myo-inosityl-2-(N-acetylcysteinyl)amido-2-deoxy-α-D-glucopyranoside.

FIG. 1B is a schematic representation of the reaction wherein MSH is alkylated (R=alkylating group) to MSR and broken down by enzyme mycothiol S-conjugate amidase (MCA) to form 1-D-myo-inosityl-2-amino-2-deoxy-α-D-glucopyranoside (GlcN-Ins) and a mercapturic acid (Ac-CysR).

FIG. 1C is a schematic representation showing hydrolysis of bimane derivative (MSmB) formed by alkylation of mycothiol by monobromobimane (mBBr), which is cleaved to produce GlcN-Ins and the bimane derivative of N-acetylcysteine (AcCySmB), a mercapturic acid.

FIG. 6 is a chart showing alignment of the amino acid sequences of five homologs of *M. smegmatis* mycothiol S-conjugate amidase designated by the genes that encode them: Rv1082=the amidase gene from *M. tuberculosis* H37Rv (SEQ ID NO:16); *M. leprae* (SEQ ID NO:17); lmbE=the lincomycin biosynthesis gene E from *Streptomyces lincolnensis* (SEQ ID NO:13; rifO=rifamycin biosynthesis gene O from *Amycolaptosis mediterranei* (SEQ ID NO:14); Rv1170=an acetyl glucosaminyl inositol (N-Acetyl-1-D-myo-Inosityl-2 amino-2 deoxy-α-D-glucopyranoside) deacetylase from *M. tuberculosis* H37Rv (SEQ ID NO:15) (G. L. Newton et al., *J Bacterol.* 182(24): 6958–6963 (2000).

FIG. 9 is a chart showing alignment of the amino acid sequences of the mycothiol S-conjugate amidases of *M. smegmatis* mc2 155 (SEQ ID NO:1) (source TIGR) and *M. tuberculosis* H37Rv (Rv1082) (SEQ ID:7) (Source Sanger Center). The two sequences are 78% identical overall and the N-terminal 20 amino acids are 100% identical (SEQ ID:8).

FIG. 10 shows the nucleic acid sequences encoding the mycothiol S-conjugate amidase of *M. smegmatis* (SEQ ID NO:6) and *M. tuberculosis* (SEQ ID:9)

DETAILED DESCRIPTION OF THE INVENTION

Figure 2:
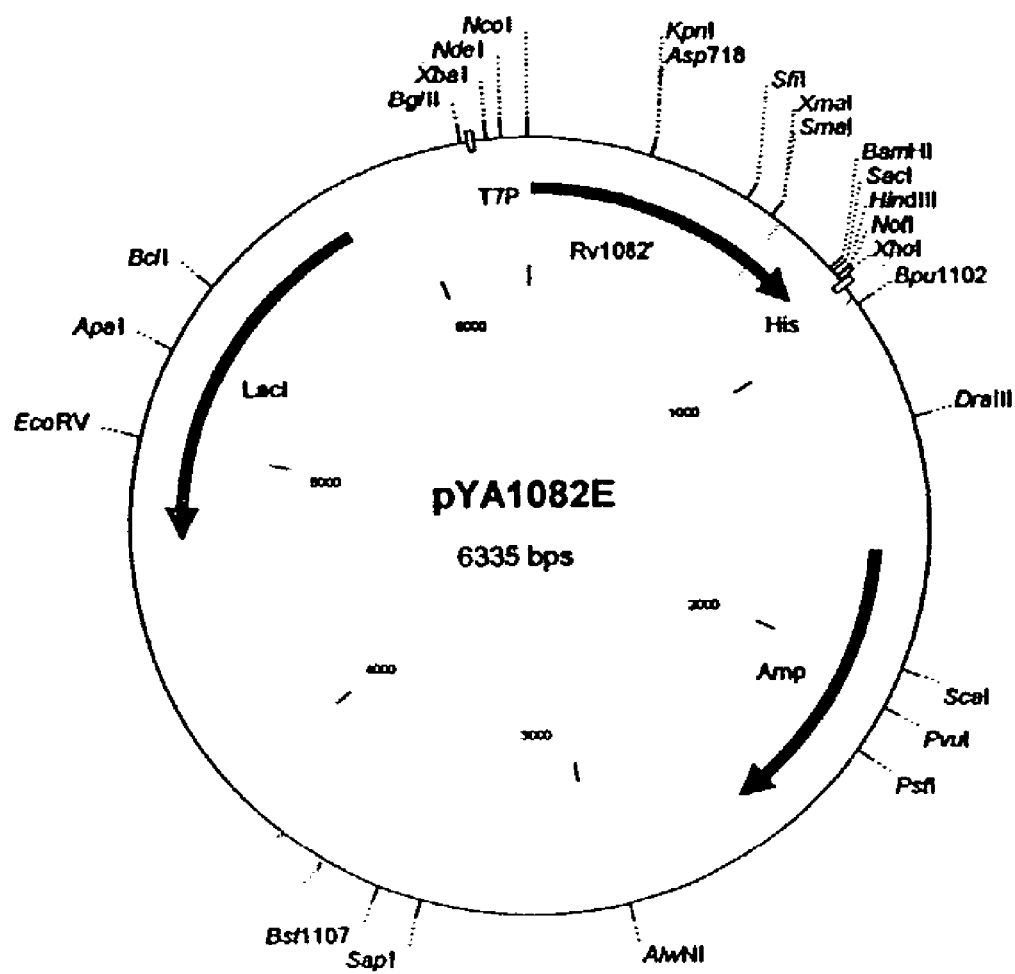
FIG. 2 is a schematic representation of vector pYA1082E.

In accordance with the present invention, there are provided a family of purified acyl glucosaminyl inositol amidase polypeptides with enzymatic amidase activity for glucosaminyl inositol (GlcN-Ins)-containing substrates. The invention acyl glucosaminyl inositol amidases are characterized by having an N-terminal region with an amino acid sequence with at least 80% sequence identity to amino acid sequence MSELRLMAVHAHPDDESSKG (SEQ ID NO: 2), four highly conserved domains wherein three of the domains contain conserved histidine residues, and amidase activity against glucosaminyl inositol-containing amides.

In preferred embodiments the invention polypeptides have enzyme activity as an amide hydrolase and the three histidine-containing conserved regions are selected from V/F-HAHPDD (SEQ ID NO:3) of domain 1, D/HPDHI/V (SEQ ID NO:4) of domain 3, and ALX-A/S-H-A/V-T/S-Q (SEQ ID NO:5) of domain 4 as shown in FIG. 6 and FIG. 9, or any combination of any two or more thereof.

A subset of the acyl glucosaminyl inositol amidases are referred to herein as S-conjugate amidases, whose substrate is an S-conjugate containing amide. As used herein, the term "S-conjugate" means that the molecule is a thioether or thioester containing two chemical moieties joined by a sulfur (i.e., —S—) moiety. In a preferred embodiment the S-conjugate molecule is derived from mycothiol (FIG. 1A) by the reaction shown in FIG. 1B, wherein RX is an electrophile and R is an alkyl or alkyloid moiety. However, the acyl glucosaminyl inositol amidases of the invention acyl glucosaminyl inositol amidase family do not require a sulfur-containing amide substrate and instead cleave an GlcN-Ins-containing amide substrate.

As used herein, the terms "GlcN-Ins-containing amide" and "glucosaminyl inositol-containing amide" are interchangeable when used to describe a substrate molecule for which a member of the invention family of amidases have enzymatic activity, resulting in cleavage of the molecule. Similarly, the term "amide-containing S-conjugate" and "S-conjugate-containing amide" are interchangeable when used to describe a substrate molecule for which a member of the invention S-conjugate amidases have enzymatic activity, resulting in cleavage of the molecule. If a particular member of the invention family of polypeptide amidases is an amide hydrolase, cleavage of the substrate molecule will form breakdown products wherein one product is a carboxylic acid, (e.g., a carboxylic acid containin at least one sulfur moiety) and the other product is a amine (e.g., GlcN-Ins). If the substrate is a mycothiol-derived S-conjugate amide of the type illustrated in FIG. 1B, one of the breakdown products will be 1-D-myo-inosityl-2-amino-2-deoxy-α-D-glucopyranoside (GlcN-Ins) and the other breakdown product will be a sulfur-containing carboxylic acid, such as a mercapturic acid. AcCys S-conjugates are termed mercapturic acids, the final excreted product in the mercapturic acid pathway of glutathione-dependent detoxification in mammals (J. L. Stevens, et al., (1989) in *Glutathione: Chemical, Biochemical, and Medical Aspects—Part B* (D. Dolphin, et al.) pp 45–84, John Wiley & Sons, et al.).

It has been discovered that invention acyl glucosaminyl inositol amidases participate in a pathway of detoxification in bacteria, especially antibiotic-producing bacteria, and that the detoxification pathway is dependent on in vivo production of a protein acyl glucosaminyl inositol amidase by such bacteria. However, pathogenic actinomycetes (that do not produce an antibiotic) also contain a gene encoding an acyl glucosaminyl inositol amidase that becomes activated in the presence of antibiotics administered to a host, for example in treatment of a disease caused by the pathogenic actinomycetes. Thus, the gene(s) encoding the invention family of amidases are a family of antibiotic-resistance genes.

More particularly, it has been discovered that mycothiol (1-D-myo-inosityl-2-(N-acetylcysteinyl)amido-2-deoxy-α-D-glucopyranoside) (MSH) is present in a variety of actinomycetes and plays an essential role in a pathway of detoxification in such bacteria. Mycothiol is comprised of N-acetylcysteine (AcCys) amide linked to 1-D-myo-inosityl-2-amino-2-deoxy-α-D-glucopyranoside (GlcN-Ins) and is the major thiol produced by most actinomycetes. In the mycothiol-dependent detoxification process in actinomycetes, an alkylating agent is converted to a S-conjugate of mycothiol, the latter is cleaved to release a mercapturic acid, and the mercapturic acid is excreted from the cell. This process has similarities to the mercapturic acid pathway for glutathione-dependent detoxification in higher eukaryotes (J. L. Stevens, et al. (1989) supra.) but involves fewer steps.

An S-conjugate amidase responsible for cleavage of the S-conjugate of mycothiol has been purified from *M. smegmatis* (SEQ ID NO:1 shown in FIG. 9) and was found to be located at amino acid residues 5717 through 4858 of a plasmid having Sanger Center Accession No. GMS-684. The N-terminal region 20 residues of this newly discovered S-conjugate amidase was determined as shown in SEQ ID NO:2. The nucleic acid sequence that encodes the *M. smegmatis* S-conjugate amidase (SEQ ID NO: 6) is found at nucleic acid residues 3854 to 6717 of the plasmid having Sanger Center Accession No. GMS-684, shown in FIG. 10.

An open reading frame encoding an identical predicted amino-terminal amino acid sequence was also identified in the *M. tuberculosis* genome (FIG. 9). The Rv1082 gene (mca) from *M. tuberculosis* was inserted into vector pYA1082E (FIG. 2) and expressed in *E. coli*, and the expressed protein was shown to have substrate specificity similar to the invention amidase from *M. smegmatis*. These results indicate that mycothiol and mycothiol S-conjugate amidases play an important role in the detoxification of alkylating agents and antibiotics.

When *M. tuberculosis* S-conjugate amidase was used to search genomic databases, few proteins with similar size were identified as close homologs. Interestingly, all identified homologous proteins were putative with heretofore unknown function. As expected from the enzymatic activity utilizing mycothiol-S-conjugates as substrates for *M. smegmatis* and *M. tuberculosis*-derived amidases, most of the homologous non-mycobacterial proteins were found in actinomycetes which produce mycothiol. Homolog genes encoding S-conjugate amidases were found to be located within antibiotic synthesis operons of the antibiotic producers *Streptomyces lincolnensis, Amycolatopsis mediterranei, Amycolatopsis orientalis, Streptomyces lavendulae, Streptomyces coelicolor, Streptomyces rochei*, and the polyketide erythromycin antibiotic producer *Saccharopolyspora erythraea*.

The sequence alignment also provides information that was found by screening for S-conjugate amidase homologs against bacterial genomic sequence databases. Within *M. tuberculosis* an open reading frame, which encodes for homolog Rv1170, was identified. In other mycobacteria, such as *M. leprae*, a member of invention family of acyl glucosaminyl inositol amidases is encoded by ORF 05988 located in the cosmid B1740, and the *M. avium* homolog was represented in a contig 9 in the TIGR genome databases. An additional S-conjugate amidase homolog was also identified in the *M. bovis* genome database that is currently underway at the Sanger Centre. Interestingly two other bacteria, *Corynebacterium diphtheria* and *Deinococcus radiodurans*, were also found to encode acyl glucosaminyl inositol amidase homologs. Thus, protein homologs in GenBank (National Center for Biotechnology Information, Building 38A, Room 8N805, Bethesda, Md. 20894) for which function had not previously been identified were identified as members of the invention family of acyl glucosaminyl inositol amidases by comparative analysis. Four of these proteins are putative actinomycetes proteins encoded within the lincomycin, erythromycin, mitomycin and the rifamycin antibiotic biosynthetic operons.

To identify functional domains within the group of homologs, a search for known protein motifs or domains was performed against protein databases. No known functional domains were identified. However, ClustalW alignment (See FIG. 6) of M. tuberculosis mycothiol S-conjugate amidase against several homologs, revealed at least four major domains that are highly conserved among members of the invention family of polypeptide amidases. Three out of the four domains contain conserved histidine residues: V/F-HAHPDD (SEQ ID NO:3) of domain 1, D/HPDHI/V (SEQ ID NO:4) of domain 3, and ALX-A/S-H-A/V-T/S-Q (SEQ ID NO:5) of domain 4. These conserved domains are thought to be involved in the amide hydrolysis and binding to glucosaminyl inositol. Furthermore, this alignment clearly demonstrates that members of invention family of acyl glucosaminyl inositol amidase proteins are highly conserved and share a high degree of identity throughout the whole protein. Those of skill in the art will be able to identify additional members of the acyl glucosaminyl inositol amidase family by performing similar homology searches and sequence alignments using available genomic databases, and the like, in conjunction with any of a number of sequence alignment programs commercially available. Genes coding for mycothiol S-conjugate amidase appear to be present in all of the mycobacterial genomes presently available and it seems likely that homologs will be found in other mycothiol-producing actinomycetes.

Figure 5:
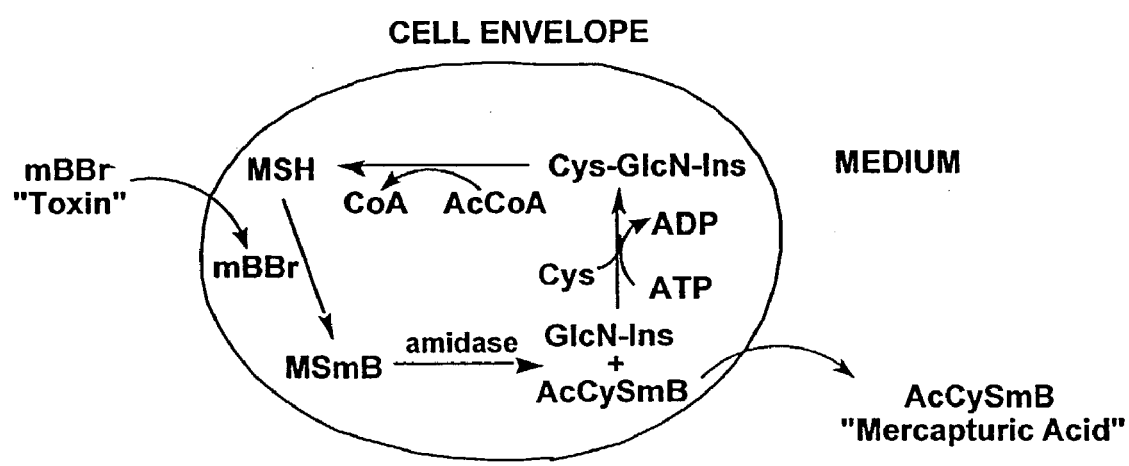
FIG. 5 is a schematic drawing showing MSH-dependent detoxification of mBBr or other toxins by mycobacteria.

Members of invention family of acyl glucosaminyl inositol amidases are formed in vivo by bacteria as part of a detoxification pathway, usually in antibiotic-producing bacteria, and most usually in bacteria characterized by intracellular production of mycothiol. When *Mycobacterium smegmatis* was treated with the alkylating agent monobromobimane (mBBr), the cellular mycothiol was converted to its bimane derivative (MSmB) (FIG. 1C). The latter was rapidly cleaved to produce GlcN-Ins and the bimane derivative of N-acetylcysteine (AcCySmB), a mercapturic acid that was rapidly exported from the cells into the medium. The other product of cleavage, GlcN-Ins, was retained in the cell and utilized in the resynthesis of mycothiol. This reaction scheme is shown in FIG. 5.

Figure 7:
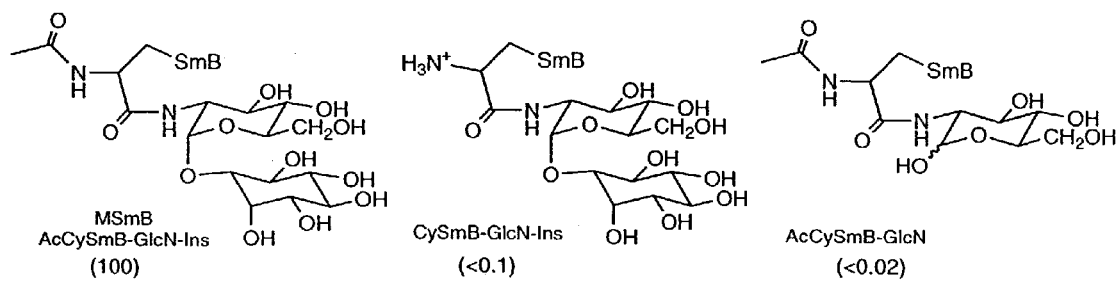
FIG. 7 is a chart showing chemical structures of various substrates for mycothiol S-conjugate amidase with changes in the structure of the mycothiol moiety. MSmB activity is defined as 100%.

The substrate specificity of the amidase reaction was examined using various mycothiol related compounds (Table 2; FIG. 7). A very low but measurable activity was found with mycothiol under these conditions. When mycothiol was examined at 2 mM, a concentration comparable to the cellular level of mycothiol (S. J. Anderberg, et al. (1998) supra.), under conditions otherwise the same as for Table 2 the rate of GlcN-Ins formation was 14±1 nmol/min/mg, or 0.3% of the rate with 0.1 mM MSmB. Mycothiol disulfide was a better substrate than mycothiol but still <1% as reactive as MSmB. Removal of the acetyl group from MSmB resulted in a $10^3$-fold reduction in rate and removal of the inositol residue produced a $>10^4$-fold loss of activity (FIG. 7). The invention amidase exhibited substantial activity with a wide range of S-conjugates other than MSmB, including the S-conjugate of the antibiotic cerulenin (S. Omura (1981) *Meth. Enzymol.* 72:520–532) which serves as an example of a naturally occurring substrate (Table 2, FIG. 8).

Tests were also conducted to determine whether mycothiol inhibits the cleavage of 100 μM MSmB by invention S-conjugate amidase. The amidase activity was decreased by 30±3, 48±3, and 89±3% (n=2) at 1, 3, and 10 mM mycothiol, respectively. This suggests that cellular levels of mycothiol could produce significant inhibition of the monomeric amidase, the presumed form under these assay conditions.

Purified *M. smegmatis* mycothiol S-conjugate amidase was assayed for cysteine:GlcN-Ins ligase activity, a mycothiol biosynthesis enzyme (C. Bornemann, et al. (1997) supra.). The reaction utilizes ATP to drive formation of an amide bond of the type hydrolyzed by invention S-conjugate amidase. The purified amidase was incubated with ATP, cysteine and GlcN-Ins, and the product, Cys-GlcN-Ins, was assayed by HPLC as the bimane derivative (S. J. Anderberg, et al. (1998) supra.). The purified amidase (0.044 μg) gave <0.33 nmol/min/mg Cys-GlcN-Ins at a protein concentration where the amidase reaction rate for 30 μM MSmB was ~3000 nmol/min/mg. As a positive control the ligase reaction was also assayed for a dialyzed crude extract from *M. smegmatis* and 0.36 nmol/min/mg protein Cys-GlcN-Ins was formed in accord with previous reports (Newton, et al. (1999), supra., S. J. Anderberg, et al. (1998) supra.). Thus, invention S-conjugate amidase does not appear to be involved in mycothiol biosynthesis since it has no significant ability to catalyze ATP-dependent ligation of cysteine with GlcN-Ins. It therefore does not appear to be a bifunctional enzyme analogous to the glutathionylspermidine synthetase/amidase which catalyzes both the biosynthesis and degradation of glutathionylspermidine in *E. coli* (D. S. Kwon, et al. (1997) *J. Biol. Chem.* 272:2429–2436) and in *Crithidia fasciculata* (E. Tetaud, et al. (1998) *J. Biol. Chem.* 273: 19383–19390). Attempts to detect mycothiol S-transferase activity in extracts of *M. smegmatis* using 1-chloro-2,4-dinitrobenzene with 1 mM MSH and monochlorobimane with 0.1 mM MSH did not produce significant activity (data not shown).

*E coli* has no mycothiol metabolism and is not expected to contain mycothiol conjugate amidase endogenous proteins that would give background to these assays. The amidase activity of the *M. tuberculosis*-derived S-conjugate amidase expressed in *E. coli* was found to be associated with the insoluble cell pellet material. Using 0.1 mM MSmB as substrate, the resolublilzed crude protein extract was found to produce 4.1±0.05 nmoles/min/mg protein GlcN-Ins and 5.4±0.3 nmoles/min/mg protein AcCysmB. When using 0.1 mM MSH as substrate <0.0023 nmoles/min/mg protein GlcN-Ins was produced by the same extract. The products of the reaction and the >2,000 fold rate enhancement for conjugates of MSH relative to the free thiol is very similar to invention S-conjugate amidase purified from *M. smegmatis*.

Based on these activity studies, which are described more fully in the Examples hereinbelow, it is concluded that acyl glucosaminyl inositol amidases (for example, S-conjugate) amidases participate in detoxification of antibiotics or the antibiotic biosynthesis by-products in actinomycetes and other bacteria. In disease states characterized by the presence of such pathogenic bacteria (e.g., bacterial infections), therapeutic antibiotics administered to the subject being treated may have limited effectiveness in treating the disease because of innate resistance of the pathogenic bacterium to antibiotics subject to such a detoxification pathway. Such a bacterium may prove resistant to the therapeutic antibiotic administered to the subject hosting the bacterium. The studies described herein indicate that pathogenic bacteria particularly susceptible to such resistance are pathogenic actinomycetes, such as those derived from *M. smegmatis, M. tuberculosis, M. leprae, M. bovis, Corynebacterium diph-*

*theria, Actinomycetes israelii, M. avium*, and the like, that can produce a native GlcN-Ins-containing amide.

Accordingly, in another embodiment of the present invention, there are provided methods for identifying an inhibitor of acyl glucosaminyl inositol amidase activity by contacting a candidate compound with an acyl glucosaminyl inositol amidase or a polynucleotide encoding the amidase in the presence of an GlcN-Ins-containing amide under suitable conditions and then determining the presence or absence of breakdown products of the amide indicative of amide hydrolase activity. The substantial absence of the amide hydrolase activity is indicative of a compound that inhibits activity of the amidase. For example, if the amidase is an S-conjugate amidase, the absence of mercapturic acid (AcCysR) and/or GlcN-Ins as breakdown products indicates the candidate compound is an inhibitor of the S-conjugate amidase. The inhibitor may be a polypeptide, oligonucleotide, or small molecule. When administered in treatment of a disease associated with infection of the subject with a pathogenic bacteria that produces a native acyl glucosaminyl inositol amidase in conjunction with an antibiotic (i.e., in combination therapy) the inhibitor increases the therapeutic effect of the antibiotic.

Preferably, the inhibitor is a compound, such as an anti-sense oligonucleotide, that inhibits intracellular production of the amidase. For example, the antisense oligonucleotide can be complementary to a target region in a messenger RNA that encodes a polypeptide having an amino acid sequence segment with at least 80% sequence identity to the amino acid sequence of SEQ ID NOS:2, 3, 4 or 5 and conservative variations thereof. In another embodiment the antisense oligonucleotide hybridizes under intracellular conditions with a messenger RNA that encodes a polypeptide having an N-terminal amino acid sequence as set forth in SEQ ID NO:2.

For example, in one embodiment, the candidate compound inhibits intracellular production or activity of the acyl glucosaminyl inositol amidase. A presently preferred drug candidate for screening in live bacteria for activity that inhibits intracellular production or activity of acyl glucosaminyl inositol amidase is an anti-sense oligonucleotide complementary to a target region in a messenger RNA that encodes a polypeptide having an N-terminal amino acid sequence with at least 80% sequence identity to the amino acid sequence set forth in SEQ ID NO:2, or a conservative variation thereof, for example, 85%, 90%, 95% or 100% sequence identity. Suitable conditions for conducting invention drug screening methods are well known in the art and are described, for example, in the Examples hereinbelow.

In yet another embodiment according to the present invention, there are provided methods for decreasing the antibiotic-resistance of pathogenic GlcN-Ins-amidase producing bacteria by introducing into the bacteria an inhibitor of acyl glucosaminyl inositol amidase activity. The intracellular presence of the inhibitor decreases activity of the amidase, thereby decreasing the antibiotic-resistance of the bacteria as compared with untreated control bacteria. The inhibitor can be a polypeptide, polynucleotide or oligonucleotide, or a small molecule Preferably, the inhibitor inhibits intracellular production of the amidase.

For example, the inhibitor can be an antisense oligonucleotide complementary to a target region in a messenger RNA that encodes an acyl glucosaminyl inositol amidase polypeptide that is introduced into the pathogenic GlcN-Ins-amidase producing bacteria, using methods known in the art and as described herein. For example, the pathogenic bacteria can be contacted with an antisense oligonucleotide that hybridizes under intra cellular conditions with a messenger RNA that encodes an amino acid sequence segment with at least 80% sequence identity to the amino acid sequence of SEQ ID NOS:2, 3, 4, or 5 and conservative variations thereof or a polypeptide having an N-terminal amino acid sequence as set forth in SEQ ID NO:2.

Preferably, the pathogenic bacteria treated to reduce drug resistance according to the invention methods are actinomycetes, such as *M. smegmatis, M. tuberculosis, M. leprae, M. bovis, M. intracellulare, M. africanum, M. marinarum, M. chelonai, Corynebacterium diphtheria, Actinomycetes israelii, M. avium*, and the like.

In one embodiment, the amidase produced by the pathogenic bacteria is mycothiol S-conjugate amidase, e.g. one capable of hydrlyzing a mycothiol S-conjugate where the S-R group may be an alkyl or alkyloid group.

In still another embodiment according to the present invention, there are provided methods for increasing production of antibiotic by antibiotic-producing bacteria by contacting the antibiotic-producing bacteria with a compound that increases intracellular production by the bacteria in culture of an acyl glucosaminyl inositol amidase. The increase in intracellular production of the amidase increases the production of antibiotic by the bacteria by increasing resistance of the bacteria to the antibiotic. Generally, in industrial applications wherein antibiotic is produced from bacteria for commercial purposes, the antibiotic-producing bacteria are cultured under conditions suitable for production of the antibiotic, and the antibiotic is recovered from the culture media. The compound that increases intracellular production by the bacteria of the amidase can be a polypeptide, polynucleotide, or small molecule.

Preferably, the compound that increases intracellular production by the bacteria of the amidase is expressed intracellularly by the bacteria, preferably by actinomycetes. For example, the actinomycetes can be transformed with a polynucleotide that encodes an acyl glucosaminyl inositol and amidase and which expresses the amidase in culture. Recombinant expression of the acyl glucosaminyl inositol amidase polypeptides in cultured antibiotic-producing cells can be useful for increasing the resistance of the production cells to the toxic effect upon themselves of the antibiotics they produce. Thus, the level of antibiotics in the culture media can be increased without causing death of the production cells, thereby increasing the efficiency of industrial antibiotic production methods. Suitable polynucleotides that can be used to transform antibiotic-producing bacteria can contain nucleic acid residues 34318–35184 of the polynucleotide having GenBank Accession No. gi2896719 or encode a polypeptide containing amino acid residues 5717–4858 of Sanger Center Accession No. 684.

Suitable bacteria for use in the invention method for increasing production of antibiotics by antibiotic-producing bacteria include *Streptomyces lincolnensis, Amycolatopsis mediterranei, Amycolatopsis orientalis, Streptomyces lavendulae, Streptomyces coelicolor, Streptomyces rochei* and *Saccharopolyspora erythraea*.

In yet another embodiment according to the present invention, there are provided methods for detoxifying a toxic substance by contacting the toxic substance with bacteria transformed with a polynucleotide that encodes an acyl glucosaminyl inositol amidase and expressing the amidase in order to detoxify the toxic substance. Preferably, the bacteria is a strain currently in use for detoxification of environmental pollutants and the bacteria are transformed with a polynucleotide that encodes the amidase such that the amidase is expressed intracellularly under environmental conditions. The environmental condition may include or be a pollutant. Such environmental pollutants that may be detoxified according to invention methods include, but are not limited to 1, 2 dibromoethane, 1,2 dichloroethane, perchloroethene, trichloroethene, isoprene, and vinyl chloride. They are from pesticides, industrial degreasers, solvents, and from the production polyvinyl chloride polymers (plastics), such as a halogenated hydrocarbon, or the epoxides, such as isoprene monoxide, and the like.

In still another embodiment according to the present invention, there are provided processes for preparation of GlcN-Ins by contacting an N-acyl glucosaminyl inositol under suitable conditions with an acyl glucosaminyl inositol amidase so as to hydrolyze the amide bond therein to obtain stereochemically pure α(1 1) GlcN-Ins (1-D-myo-inosityl-2-amino-2-deoxy-α-D-glucopyranoside). Preferably the N-acyl glucosaminyl inositol is a mycothiol S-conjugate, such as the bimane derivative of mycothiol. The amidase cleaves the N-acyl glucosaminyl inositol, freeing GlcN-Ins as one of the cleavage breakdown products. GlcN-Ins has utility in conducting research regarding amidase activity and mycothiol biochemistry in bacteria, development of products and procedures for overcoming the antibiotic resistance of pathogenic bacteria, such as actinomycetes, and as a precursor for formation of acyl glucosaminyl inositol derivatives and inhibitors of amidases thereof.

A "conservative variation" in an amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an amidase polypeptide, resulting in modification of the structure of the polypeptide, without significantly altering its biological activity. For example, carboxyl-terminal amino acids that are not required for amidase activity can be removed.

Alternatively, an antisense oligonucleotide can be designed to hybridize under in vivo conditions with a messenger RNA that encodes a polypeptide having an N-terminal amino acid sequence as set forth in SEQ ID NO:2, or contains an amino acid segment as set forth in SEQ ID NOs:3, 4, or 5, or a conservative variation thereof.

The antisense oligonucleotide can comprises from about 10 to about 60 nucleic acid residues, for example from 10 to about 50, or from 10 to about 40, 30 or 20 nucleic acid residues. "Hybridization" refers to the process by which a nucleic acid strand joins with a complementary strand through base pairing. Hybridization reactions can be sensitive and selective so that a particular sequence of interest will join with a complementary strand even in samples in which it is present at low concentrations. Suitable intracellular conditions for hybridization of an antisense oligonucleotide to messenger RNA will be determined by the particular bacterium used in the invention method. In general, the pH, temperature and salt concentration must be comparable to intracellular conditions in the test bacterium.

Biologically functional viral and plasmid DNA vectors capable of expression and replication in a host are known in the art. Such vectors are used to incorporate DNA sequences of the invention. In general, expression vectors containing promoter sequences which facilitate the efficient transcription of the inserted eukaryotic genetic sequence are used in connection with the host. The expression vector typically contains an origin of replication, a promoter, and a terminator, as well as specific genes which are capable of providing phenotypic selection of the transformed cells.

In addition to expression vectors known in the art such as bacterial, yeast and mammalian expression systems, baculovirus vectors may also be used. One advantage to expression of foreign genes in this invertebrate virus expression vector is that it is capable of expression of high levels of recombinant proteins, which are antigenically and functionally similar to their natural counterparts. Baculovirus vectors and the appropriate insect host cells used in conjunction with the vectors will be known to those skilled in the art.

The term "recombinant expression vector" refers to a plasmid, virus or other vehicle known in the art that has been manipulated by insertion or incorporation of the invention acyl glucosaminyl inositol amidase genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

The isolation and purification of host cell expressed polypeptides of the invention may be by any conventional means such as, for example, preparative chromatographic separations and immunological separations such as those involving the use of monoclonal or polyclonal antibody.

Transformation of the host cell with the recombinant DNA may be carried out by conventional techniques well known to those skilled in the art. Where the host is prokaryotic, such as E. coli, competent cells which are capable of DNA uptake can be prepared from cells harvested after exponential growth and subsequently treated by electroporation or the $CaCl_2$ method using procedures well known in the art. Alternatively, $MgCl_2$ or RbCl could be used.

Where the host used is a eukaryote, various methods of DNA transfer can be used. These include transfection of DNA by calcium phosphate-precipitates, conventional mechanical procedures such as microinjection, insertion of a plasmid encased in liposomes, or the use of virus vectors. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Examples of mammalian host cells include COS, BHK, 293, and CHO cells.

Eukaryotic host cells may also include yeast. For example, DNA can be expressed in yeast by inserting the DNA into appropriate expression vectors and introducing the product into the host cells. Various shuttle vectors for the expression of foreign genes in yeast have been reported (Heinemann, J. et al., Nature, 340:205, 1989; Rose, M. et al., Gene, 60:237, 1987).

The invention provides antibodies which are specifically reactive with invention amidase polypeptides or fragments thereof.

Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495, 1975; Current Protocols in Molecular Biology, Ausubel, et al., ed., 1989). Monoclonal antibodies specific for acyl glucosaminyl inositol amidase polypeptide can be selected, for example, by screening for hybridoma culture supernatants which react with acyl glucosaminyl inositol amidase polypeptides, but do not react with other bacterial amidases.

Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495, 1975; Current Protocols in Molecular Biology, Ausubel, et al., ed., 1989).

The term "antibody" as used in this invention includes intact molecules as well as fragments thereof, such as Fab, F(ab')$_2$ and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to acyl glucosaminyl inositol amidase polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated herein by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

In yet other preferred embodiments, the recombinant acyl glucosaminyl inositol amidase polypeptide is a fusion protein further comprising a second polypeptide portion having an amino acid sequence from a protein unrelated the acyl glucosaminyl inositol amidase. Such fusion proteins can be functional in a two-hybrid assay.

Another aspect of the present invention provides a substantially pure nucleic acid having a nucleotide sequence which encodes an acyl glucosaminyl inositol amidase polypeptide, or a fragment thereof, having an amino acid sequence at least 60% homologous to one of SEQ ID NOs:2, 3, 4 or 5. In a more preferred embodiment, the nucleic acid encodes a protein having an amino acid sequence at least 80% homologous to SEQ ID NO:2, more preferably at least 90% homologous to SEQ ID NO:2, and most preferably at least 95% homologous to SEQ ID NO:2.

In another embodiment, the nucleic acid hybridizes under stringent conditions to a nucleic acid probe corresponding to at least 12 consecutive nucleotides encoding SEQ ID NO:3; more preferably to at least 20 consecutive nucleotides encoding SEQ ID NO:3; more preferably to at least 40 consecutive nucleotides encoding SEQ ID NO:3.

In a further embodiment, the nucleic acid hybridizes under stringent conditions to a nucleic acid probe corresponding to at least 12 consecutive nucleotides encoding SEQ ID NO:4; more preferably to at least 20 consecutive nucleotides encoding SEQ ID NO:4; more preferably to at least 40 consecutive nucleotides encoding SEQ ID NO:4.

In yet a further embodiment, the nucleic acid hybridizes under stringent conditions to a nucleic acid probe corresponding to at least 12 consecutive nucleotides encoding SEQ ID NO:5; more preferably to at least 20 consecutive nucleotides encoding SEQ ID NO:5; more preferably to at least 40 consecutive nucleotides encoding SEQ ID NO:5.

Furthermore, in certain embodiments, the acyl glucosaminyl inositol amidase nucleic acid will comprise a transcriptional regulatory sequence, e.g. at least one of a transcriptional promoter or transcriptional enhancer sequence, operably linked to the acyl glucosaminyl inositol amidase-gene sequence so as to render the recombinant acyl glucosaminyl inositol amidase gene sequence suitable for use as an expression vector.

The present invention also features transgenic non-human organisms, e.g. bacteria which either express a heterologous S-conjugate amidase gene, or in which expression of their own acyl glucosaminyl inositol amidase gene expression is disrupted. Such a transgenic organism can serve as an model for studying acyl glucosaminyl inositol amidase activity and for screening for compounds that inhibit acyl glucosaminyl inositol amidase activity in bacteria.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence encoding one of the amino acid sequences encompassed by SEQ ID NOs:2, 3, 4 or 5, or naturally occurring mutants thereof.

Yet another aspect of the invention pertains to a peptidomimetic which binds to an acyl glucosaminyl inositol amidase polypeptide and inhibits its binding to S-conjugate-containing amide substrate. For example, a preferred peptidomimetic is an analog of a peptide having the sequence of one of the SEQ ID NOs. 1, 2, 3, 4, or 5. Non-hydrolyzable peptide analogs of such residues can be generated using, for example, benzodiazepine, azepine, substituted gama-lactam rings, keto-methylene pseudopeptides, beta-turn dipeptide cores, or beta-aminoalcohols.

Other features and advantages of the invention will be apparent from the detailed description herein, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press:1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid comprising an open reading frame encoding an invention acyl glucosaminyl inositol amidase, including both exon and (optionally) intron sequences. The term "intron" refers to a DNA sequence present in a given acyl glucosaminyl inositol amidase gene which is not translated into protein and is generally found between exons.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "transfection" or "transforming" and grammatical equivalents thereof, refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of one of the invention family of acyl glucosaminyl inositol amidases.

"Cells" or "cell cultures" or "recombinant host cells" or "host cells" are often used interchangeably as will be clear from the context. These terms include the immediate subject cell which expresses the cell-cycle regulatory protein of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant acyl glucosaminyl inositol amidase polypeptide.

As used herein, the term "vector" refers to a nucleic acid molecule capable of transporting another nucleic acid to which it has been linked. The term "expression vector" includes plasmids, cosmids or phages capable of synthesizing the subject acyl glucosaminyl inositol amidase polypeptide encoded by the respective recombinant gene carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein coding sequences with which they are operably linked. In preferred embodiments, transcription of a recombinant acyl glucosaminyl inositol amidase gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

As used herein, a "transgenic organism" is any organism, preferably a bacteria in which one or more of the cells of the organism contain heterologous nucleic acid introduced by way of human intervention, such as by transgenic techniques well known in the art. The nucleic acid is introduced into the cell by way of deliberate genetic manipulation, such as by microinjection or by infection with a recombinant virus or a vector. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic organisms described herein, the transgene causes cells to express a recombinant form of the subject acyl glucosaminyl inositol amidase polypeptides.

As used herein, the term "transgene" means a nucleic acid sequence (encoding, e.g., an acyl glucosaminyl inositol amidase polypeptide), which is partly or entirely heterologous, i.e., foreign, to the transgenic organism or cell into which it is introduced, or, is homologous to an endogenous gene of the transgenic organism or cell into which it is introduced, but which is designed to be inserted, or is inserted, into the organism's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

The term "evolutionarily related to", with respect to nucleic acid sequences encoding acyl glucosaminyl inositol amidase polypeptides, refers to nucleic acid sequences which have arisen naturally in an organism, including naturally occurring mutants. The term also refers to nucleic acid sequences which, while derived from a naturally occurring acyl glucosaminyl inositol amidase polypeptide, have been altered by mutagenesis, as for example, combinatorial mutagenesis, yet still encode polypeptides which have the amidase activity of an acyl glucosaminyl inositol amidase polypeptide.

One aspect of the present invention pertains to an isolated nucleic acid comprising the nucleotide sequence encoding an acyl glucosaminyl inositol amidase polypeptide, fragments thereof encoding polypeptides having acyl glucosaminyl inositol amidase activity, and/or equivalents of such nucleic acids. The term nucleic acid as used herein is intended to include such fragments and equivalents. The term equivalent is understood to include nucleotide sequences encoding functionally equivalent acyl glucosaminyl inositol amidase polypeptides or functionally equivalent peptides having an activity of an acyl glucosaminyl inositol amidase polypeptide such as described herein. Equivalent nucleotide sequences will include sequences that differ by one or more nucleotide substitutions, additions or deletions, such as allelic variants; and will also include sequences that differ from the nucleotide sequence encoding native acyl glucosaminyl inositol amidases due to the degeneracy of the genetic code. Equivalents will also include nucleotide sequences that hybridize under stringent conditions (i.e., equivalent to about 20–27° C. below the melting temperature of the DNA duplex formed in about 1 M salt) to the nucleotide sequence of an acyl glucosaminyl inositol amidase gene, such as that as set forth in nucleic acid residues 34318–35184 of GenBank Accession No. gi3256022 or the polynucleotide encoding amino acids residues 5717–4858 of Sanger Center plasmid GMS-684 (SEQ ID NO:1), particularly those segments encoding the polypeptides shown in one of SEQ ID NOs. 2, 3, 4, or 5. In one embodiment, equivalents will further include nucleic acid sequences derived from and evolutionarily related to such nucleotide sequences The term "isolated" or "purified" as also used herein with respect to nucleic acids, such as DNA or RNA, refers to molecules separated from other DNAs, or RNAs, respectively, that are present in the natural source of the macromolecule. For example, an isolated nucleic acid encoding one of the subject acyl glucosaminyl inositol amidase polypeptides preferably includes no more than 10 kilobases (kb) of nucleic acid sequence which naturally immediately flanks the acyl glucosaminyl inositol amidase gene in genomic DNA, more preferably no more than 5 kb of such naturally occurring flanking sequences, and most preferably less than 1.5 kb of such naturally occurring flanking sequence. The term isolated or purified as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

In yet another embodiment, the nucleic acid of the invention encodes a peptide having an amino acid sequence as shown in GenBank Accession CAA17198 or amino acid residues 5717–4858 of Sanger Center Accession No. GMS-684. Preferred nucleic acids encode a peptide having a S-conjugate amidase polypeptide activity and being at least 60% homologous, more preferably 70% homologous and most preferably 80% homologous with an amino acid sequence shown in GenBank Accession CAA17198 (encoded by nucleic acid residues 34318–35184 of GenBank Accession No. gi3256022) or with amino acid residues 5717–4858 of Sanger Center Accession No. GMS-684. Nucleic acids which encode peptides having an activity of a S-conjugate amidase polypeptide and having at least about 90%, more preferably at least about 95%, and most preferably at least about 98–99% homology with such amino acid sequences are also within the scope of the invention.

Another aspect of the invention provides a nucleic acid which hybridizes under high or low stringency conditions to a nucleic acid which encodes an acyl glucosaminyl inositol amidase polypeptide having all or a portion of an amino acid sequence shown in one of SEQ ID NOs. 2, 3, 4, or 5. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids which differ from the nucleotide sequences disclosed herein due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject acyl glucosaminyl inositol amidase polypeptides will exist among prokaryotic cells. One skilled in the art will appreciate that these variations in one or more nucleotides (up to about 3–4% of the nucleotides) of the nucleic acids encoding a particular member of the acyl glucosaminyl inositol amidase polypeptide family may exist among individuals of a given species due to natural allelic variation. Any and all such nucleotide variations and resulting amino acid polymorphisms are within the scope of this invention.

Fragments of the nucleic acid encoding a biologically active portion of the subject acyl glucosaminyl inositol amidase polypeptides are also within the scope of the invention. As used herein, a fragment of the nucleic acid encoding an active portion of an acyl glucosaminyl inositol amidase polypeptide refers to a nucleotide sequence having fewer nucleotides than the nucleotide sequence encoding the full length amino acid sequence of, for example, the S-conjugate amidase polypeptides represented in nucleic acid residues 34318–35184 of GenBank Accession No. gi3256022, and which encodes a peptide which retains at least a portion of the biological activity of the full-length protein (i.e., a peptide capable of acyl glucosaminyl inositol amidase activity) as defined herein, or alternatively, which is functional as an antagonist of the amidase activity of the full-length protein. Nucleic acid fragments within the scope of the invention include those capable of hybridizing under high or low stringency conditions with nucleic acids from other species, e.g. for use in screening protocols to detect homologs of the subject acyl glucosaminyl inositol amidase polypeptides. Nucleic acids within the scope of the invention may also contain linker sequences, modified restriction endonuclease sites and other sequences useful for molecular cloning, expression or purification of such recombinant peptides.

As indicated by the examples set out below, a nucleic acid encoding a peptide having an activity of a S-conjugate amidase polypeptide may be obtained from mRNA or genomic DNA present in any of a number of antibiotic-producing or pathogenic bacteria, particularly actinomycetes, in accordance with protocols described herein, as well as those generally known to those skilled in the art. A cDNA encoding an acyl glucosaminyl inositol amidase polypeptide, for example, can be obtained by isolating total mRNA from a bacterial cell. Double stranded cDNAs can then be prepared from the total mRNA, and subsequently inserted into a suitable plasmid or bacteriophage vector using any one of a number of known techniques. A gene encoding an acyl glucosaminyl inositol amidase polypeptide can also be cloned using established polymerase chain reaction techniques in accordance with the nucleotide sequence information provided by the invention.

Another aspect of the invention relates to the use of an "antisense" isolated nucleic acid. As used herein, an "antisense" inhibition of endogenous production of an acyl glucosaminyl inositol amidase molecule is carried out by administration or in situ generation of oligonucleotide probes or their derivatives which specifically hybridize (e.g. bind) under intracellular conditions, with the cellular mRNA and/or genomic DNA encoding an acyl glucosaminyl inositol amidase polypeptide so as to inhibit expression of that protein or a constituent thereof, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the transformed cell, produces RNA which is complementary to at least a unique portion of the cellular mRNA which encodes an acyl glucosaminyl inositol amidase polypeptide. Alternatively, the antisense construct is an oligonucleotide probe which is generated ex vivo and which, when introduced into the cell causes inhibition of expression by hybridizing with the mRNA and/or genomic sequences encoding one of the subject acyl glucosaminyl inositol amidase proteins. Such oligonucleotide probes are preferably modified oligonucleotides which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense techniques have been reviewed, for example, by van der Krol et al. (1988) *Biotechniques* 6:958–976; and Stein et al. (1988) *Cancer Res* 48:2659–2668.

In addition, the oligomers of the invention may be used as reagents to detect the presence or absence of the target DNA or RNA sequences to which they specifically bind. Such diagnostic tests are described in further detail below.

This invention also provides expression vectors comprising a nucleotide sequence encoding a member of the invention family of acyl glucosaminyl inositol amidase polypeptides and operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of an acyl glucosaminyl inositol amidase polypeptide. Accordingly, the term regulatory sequence includes promoters, enhancers and other expression control elements. Exemplary regulatory sequences are described in Goeddel; Gene Expression Technology: Methods in Enzymology 185, Academic Press, San Diego, Calif. (1990). For instance, any of a wide variety of expression control sequences-sequences that control the expression of a DNA sequence when operatively linked to it may be used in these vectors to express DNA sequences encoding the acyl glucosaminyl inositol amidase polypeptides of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast .alpha.-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

As will be apparent, the subject gene constructs can be used to cause expression of the subject acyl glucosaminyl inositol amidase polypeptides in cells propagated in culture, e.g. to produce proteins or peptides, including fusion proteins or peptides, for purification. In addition, recombinant expression of the subject acyl glucosaminyl inositol amidase polypeptides in cultured antibiotic-producing cells, for example during large-scale production of antibiotics by antibiotic-producing bacteria, can be useful for increasing the resistance of the production cells to the toxic effect upon themselves of the antibiotics they produce. Thus, the level of antibiotics in the culture media can be increased without causing death of the production cells, thereby increasing the efficiency of industrial antibiotic production methods.

This invention also pertains to a host cell transfected with a recombinant acyl glucosaminyl inositol amidase gene in order to express a polypeptide having an activity of an acyl glucosaminyl inositol amidase polypeptide. The host cell may be any prokaryotic or eukaryotic cell. For example, an acyl glucosaminyl inositol amidase polypeptide of the present invention may be expressed in bacterial cells such as *E. coli*, insect cells (baculovirus), yeast, or mammalian cells. Other suitable host cells are known to those skilled in the art.

Another aspect of the present invention concerns recombinant acyl glucosaminyl inositol amidase polypeptides which are encoded by genes which have the amidase activity of an acyl glucosaminyl inositol amidase polypeptide, or which are naturally occurring mutants thereof. The term "recombinant protein" refers to a protein of the present invention which is produced by recombinant DNA techniques, wherein generally DNA encoding the acyl glucosaminyl inositol amidase polypeptide is inserted into a suitable expression vector which is in turn used to transform a host cell to produce the heterologous protein. Moreover, the phrase "derived from", with respect to a recombinant gene encoding the recombinant acyl glucosaminyl inositol amidase polypeptide, is meant to include within the meaning of "recombinant protein" those proteins having an amino acid sequence of a native acyl glucosaminyl inositol amidase polypeptide, or an amino acid sequence similar thereto which is generated by mutations including substitutions and deletions of a naturally occurring acyl glucosaminyl inositol amidase polypeptide of a organism.

The present invention further pertains to methods of producing the subject acyl glucosaminyl inositol amidase polypeptides. For example, a host cell transfected with expression vector encoding one of the subject acyl glucosaminyl inositol amidase polypeptide can be cultured under appropriate conditions to allow expression of the peptide to occur. The peptide may be secreted and isolated from a mixture of cells and medium containing the peptide. Alternatively, the peptide may be retained cytoplasmically and the cells harvested, lysed and the protein isolated. A cell culture includes host cells, media and other byproducts. Suitable media for cell culture are well known in the art. The peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for particular epitopes of the subject acyl glucosaminyl inositol amidase polypeptides.

Thus, a nucleotide sequence derived from the cloning of an acyl glucosaminyl inositol amidase polypeptide of the present invention, encoding all or a selected portion of the protein, can be used to produce a recombinant form of the protein via microbial cellular processes.

The recombinant acyl glucosaminyl inositol amidase polypeptide can be produced by ligating the cloned gene, or a portion thereof, into a vector suitable for expression in bacterial cells. Expression vehicles for production of a recombinant acyl glucosaminyl inositol amidase polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press:1989) Chapters 16 and 17. In some instances, it may be desirable to express the recombinant acyl glucosaminyl inositol amidase polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the .beta.-gal containing pBlueBac III).

This invention further contemplates a method of generating sets of combinatorial mutants of the present acyl glucosaminyl inositol amidase polypeptides, as well as truncation mutants, and is especially useful for identifying potential variant sequences (e.g. homologs) that are functional in cleaving S-conjugate amide molecules. In a representative embodiment of this method, the amino acid sequences for a population of acyl glucosaminyl inositol amidase polypeptide homologs are aligned, preferably to promote the highest homology possible. Such a population of variants can include, for example, homologs from one or more species, or homologs from the same species but which differ due to mutation. Amino acids which appear at each position of the aligned sequences are selected to create a degenerate set of combinatorial sequences. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (*), while insertional mutations in the variant relative to the reference sequence can be disregarded and left out of the sequence of the variant when aligned.

Further expansion of the combinatorial library (SEQ ID NO:12) can be made by, for example, by including amino acids which would represent conservative mutations at one or more of the degenerate positions. Inclusion of such conservative mutations can give rise to a library of potential cell-cycle regulatory sequences wherein Xaa(1) represents Ser, Thr, Asn or Gln; Xaa(2) represents Gly, Ala, Val, Leu, or Ile; Xaa(3) represents Arg, Lys or His; Xaa(4) represents Gly, Ala, Val, Leu, Ile, Asp or Glu; Xaa(5) represents Gly, Ala, Val, Leu, Ile, Asn or Gln; Xaa(6) represents Arg, Lys, His, Tyr or Phe; Xaa(7) represents Asp or Glu; Xaa(8) represents Pro, Gly, Ser or Thr; Xaa(9) represents Gly, Ala, Val, Leu, Ile, Asp or Glu; Xaa(10) represents Gly, Ala, Val, Leu, Ile, or an amino acid gap; Xaa(11) represents Gly, Ala, Val, Leu, Ile, Ser or Thr; Xaa(12) represents Phe, Tyr, Trp or an amino acid gap; Xaa(13) represents Ser or Thr; Xaa(14) represents Gly, Ala, Val, Leu, Ile, Arg, Lys or His; Xaa(15) represents Gly, Ala, Val, Leu, Ile, Ser or Thr; Xaa(16) represents Gly, Ala, Val, Leu or Ile; Xaa(17) represents Glx; Xaa(18) represents Gly, Ala, Val, Leu, Ile, Lys, His or Arg; Xaa(19) represents Arg or Gln; Xaa(20) represents Gly, Ala, Val, Leu or Ile; Xaa(21) represents Gly, Ala, Val, Leu or Ile; Xaa(22) represents Gly, Ala, Val, Leu, Ile, Lys, His or Arg; Xaa(23) represents Gly, Ala, Val, Leu, Ile, Thr or Ser; Xaa(24) represents Gly, Ala, Val, Leu, Ile, Ser, Thr or an amino acid gap, where in this context, an amino acid gap is understood to mean the deletion of that amino acid position from the polypeptide. Alternatively, amino acid replacement at degenerate positions can be based on steric criteria, e.g. isosteric replacement, without regard for polarity or charge of amino acid sidechains. Similarly, completely random mutagenesis of one or more of the variant positions (Xaa) can be carried out.

In a preferred embodiment, the combinatorial acyl glucosaminyl inositol amidase library is produced by way of a degenerate library of genes encoding a library of polypeptides which each include at least a portion of potential acyl glucosaminyl inositol amidase polypeptide sequences. For instance, a mixture of synthetic oligonucleotides can be enzymatically ligated into gene sequences such that the degenerate set of potential acyl glucosaminyl inositol amidase nucleotide sequences are expressible as individual polypeptides, or alternatively, as a set of larger fusion proteins (e.g. for phage display) containing the set of acyl glucosaminyl inositol amidase polypeptide sequences therein.

There are many ways by which the library of potential acyl glucosaminyl inositol amidase homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential acyl glucosaminyl inositol amidase sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp. 273–289; Itakura et al. (1984) Annu. Rev. Biochem. 53:323; Itakura et al. (1984) Science 198:1056; Ike et al. (1983) Nucleic Acid Res. 11:477.

A wide range of techniques are known in the art for screening gene products of combinatorial libraries made by point mutations, and, for that matter, for screening cDNA libraries for gene products having a certain property. Such techniques will be generally adaptable for rapid screening of the gene libraries generated by the combinatorial mutagenesis of acyl glucosaminyl inositol amidase homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene product was detected. Each of the illustrative assays described below are amenable to high through-put analysis as necessary to screen large numbers of degenerate sequences created by combinatorial mutagenesis techniques.

The invention also provides for reduction of the subject acyl glucosaminyl inositol amidase polypeptides to generate mimetics, e.g. peptide or non-peptide agents, which are able to mimic binding of the authentic acyl glucosaminyl inositol amidase polypeptide to a substrate S-conjugate amide molecule. Such mutagenic techniques as described above, as well as the thioredoxin system, are also particularly useful for mapping the determinants of an acyl glucosaminyl inositol amidase polypeptide which participate in protein-protein interactions involved in, for example, binding of the subject acyl glucosaminyl inositol amidase polypeptide to a substrate. To illustrate, the critical residues of a subject acyl glucosaminyl inositol amidase polypeptide which are involved in molecular recognition of substrate can be determined and used to generate acyl glucosaminyl inositol amidase-derived peptidomimetics which bind to S-conjugate amide substrates and, like the authentic acyl glucosaminyl inositol amidase polypeptide, cleave the substrate molecule, for example by amide hydrolase activity. By employing, for example, scanning mutagenesis to map the amino acid residues of a particular acyl glucosaminyl inositol amidase polypeptide involved in binding to a substrate, peptidomimetic compounds (e.g. diazepine or isoquinoline derivatives) can be generated which mimic those residues in binding to the amidase. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in *Peptides: Structure and Function* (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J Chem Soc Perkin Trans 1:1231), and .beta.-aminoalcohols (Gordon et al. (1985) Biochem Biophys Res Commun 126:419; and Dann et al. (1986) Biochem Biophys Res Commun 134:71).

In the studies described herein, it was discovered that alkylation of mycothiol with mBBr produces the stable, fluorescent derivative MSmB which can be quantitated by HPLC (Newton, et al. (1996), Newton, et al. (1995) supra.).

However, when a pure sample of MSmB was exposed to a cell-free extract from *M. smegmatis*, the recovery of MSmB was poor and a substantial amount of AcCySmB was detected, indicating that MSmB had been cleaved by an enzyme present in the cell extract. The experiment was repeated using a partially purified cell extract and samples of the incubation mixture were analyzed at intervals for the other potential product of MSmB cleavage, GlcN-Ins, as well as for MSmB and AcCySmB. Based upon 4 determinations at >50% conversion it was found that 1.0 equivalent of MSmB (0.1 nmol) yielded 1.00±0.02 equivalent of AcCySmB and 0.80±0.08 equivalent of GlcN-Ins with the reaction proceeding to 97% conversion of MSmB in 60 min at 23° C. This established the presence in the cell extract of mycothiol S-conjugate amidase which catalyzes the reaction shown in FIG. 1C.

Figure 3:
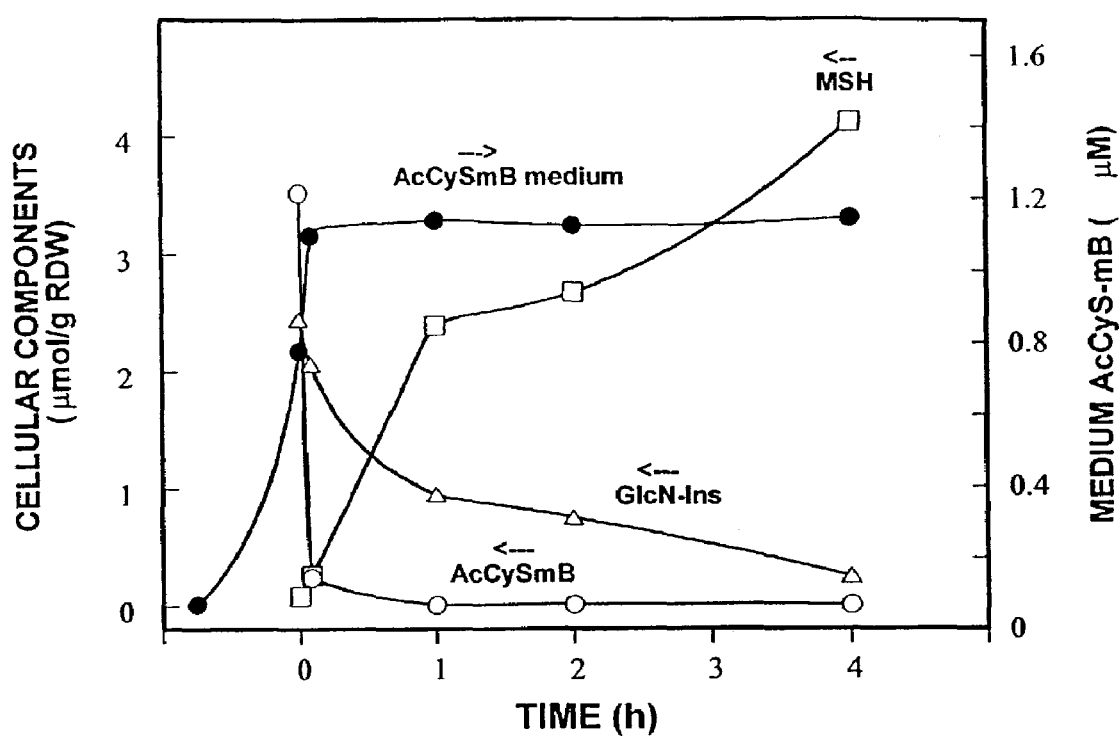
FIG. 3 is a graph showing detoxification of mBBr by exponentially growing cells of *M. smegmatis*. AcCySmB content of cells=open circle; AcCySmB content of medium=dark circle; cellular content of MSH=open square; cellular content of GlcN-Ins=open triangle.

Since mBBr is known to penetrate cells rapidly and to convert intracellular thiols to their bimane derivatives (Newton, et al. (1995) supra.), the fate of mycothiol in *M. smegmatis* cells treated with mBBr was examined to ascertain whether the reaction shown in FIG. 1C occurs in vivo. A logarithmic phase culture of *M. smegmatis* was cooled on ice to ~3° C. to reduce enzymatic reactions prior to reaction with 0.5 mM mBBr. Excess reagent was reacted with 2-mercaptoethanol and the cells were pelleted, washed, and resuspended in a small amount of ice cold medium. The cells were diluted with prewarmed medium and replaced in the shaking incubator at 37° C. (time, t=0). Samples were removed and analyzed for intracellular and extracellular mycothiol related compounds over a 4 h interval (FIG. 3).

At t=0 no significant mycothiol or MSmB was found in cells or medium but both contained significant levels of AcCySmB, indicating that the mycothiol had fully reacted with mBBr and hydrolyzed to the corresponding AcCySmB derivative (FIG. 3), much of this conversion presumably having occurred during the initial incubation on ice. At t=0, 90 mmol per 100 mL (3.5 μmol per g RDW) of AcCySmB was present in the cells and 160 nmol per 100 mL was found in the medium. Within 5 min the cellular AcCySmB level had fallen to 8 mmol per 100 mL and the medium level increased to 220 mmol per 100 mL. Subsequent analyses found essentially all of the AcCySmB in the medium at a level of 225–230 nmol per 100 mL, accounting for 80–90% of the original cellular mycothiol content. No MSmB appears to be exported from cells as <1 nmol per 100 mL (<0.5%) was detected in the medium or the cell washes.

Figure 4:
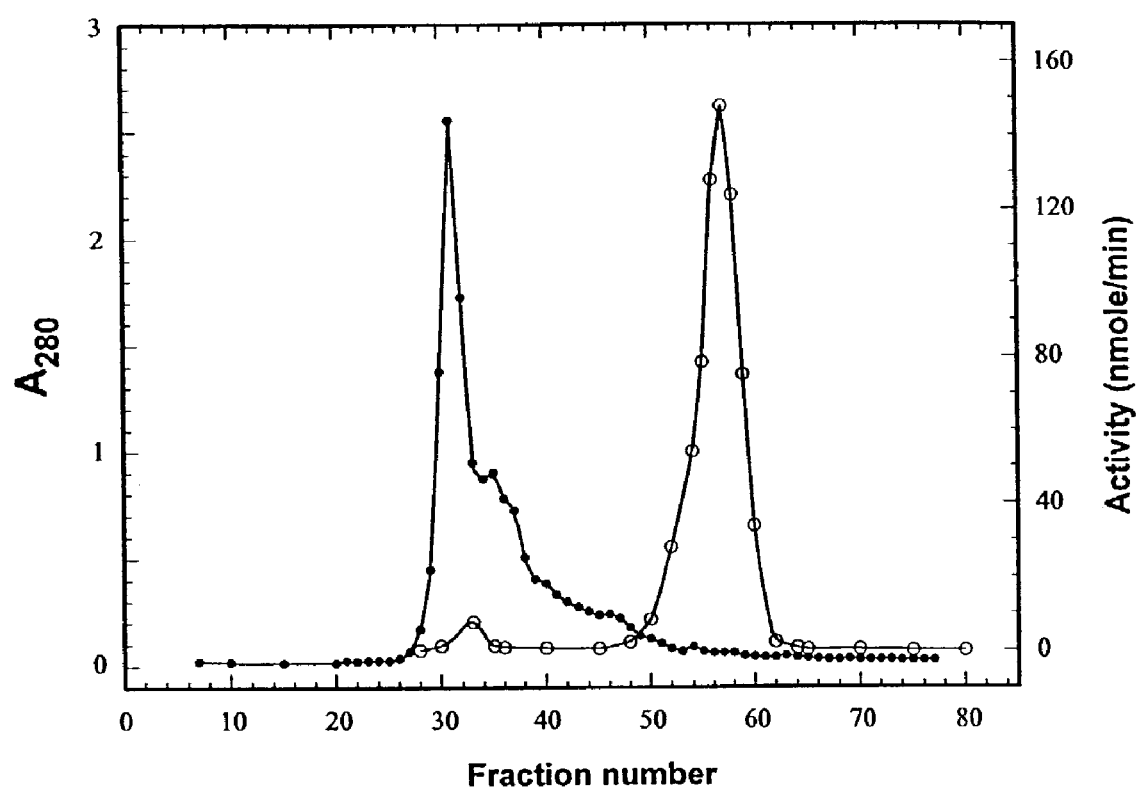
FIG. 4 is a graph showing the final step in purification of *M. smegmatis* amidase from Sephadex G-100 chromatography of highest specific activity fractions from Phenyl-Sepharose chromatography. A280=absorbance 280 nm, dark circles; amidase activity=open circles.

The cellular level of GlcN-Ins was comparable to that of AcCySmB at t=0 (FIG. 3) and represented a ~25-fold increase above the normal level of ~0.1 μmol GlcN-Ins per g RDW (S. J. Anderberg, et al. (1998) supra.). The GlcN-Ins level declined slowly over the 4 h incubation while the mycothiol content increased from a nearly undetectable level at t=0 to about half the normal cellular level after 4 h (FIG. 4). These results indicate that GlcN-Ins produced by cleavage of MSmB is retained by the cell and is utilized in the resynthesis of mycothiol. No detectable low molecular weight bimane derivatives remained in the cells at 4 h. During the 4 h incubation the $A_{600}$ value initially decreased ~15% but then recovered its initial value of 1.2. Continued incubation at 37 C resulted in a further increase to 1.6 at 8.5 h and a final $A_{600}$ ~2.6 at 30 h. Thus, at least one cell doubling occurred subsequent to the treatment with mBBr and the cells entered stationary phase at a normal cell density.

Although the mammalian glutathione-dependent and the mycobacterial mycothiol-dependent systems produce the same final product, the mammalian system is more complex. In mammals, intracellular conversion of alkylating agents to glutathione S-conjugates is catalyzed by glutathione S-transferases (B. Ketterer, et al. (1988) *in Glutathione Conjugation: Mechanisms and Biological Significance* (H. Sies, et al. Eds.) pp 73–135, London, B. Mannervik, et al. (1988) *CRC Crit. Rev. Bioch.* 23:283–337) and occurs in various tissues. Glutathione S-conjugates are exported to the plasma and transported to other tissues, notably kidney and liver, where they are extracellularly degraded by γ-glutamyltranspeptidase to CySR-Gly and the latter cleaved by a dipeptidase to produce a cysteine S-conjugate, CySR (J. L. Stevens, et al. (1989) supra.). CySR is imported and acetylated by acetyl CoA to produce a mercapturic acid (AcCySR) which is ultimately excreted in urine and bile.

Although the final excreted product is the same in the two systems, the detailed biochemistry is different. Intracellular degradation of MSmB is advantageous for a single cell organism because the hydrophilic GlcN-Ins produced is retained by the cell and can be utilized for resynthesis of mycothiol. The more hydrophobic mercapturic acid, AcCySmB, is rapidly lost from cell. This loss may occur by passive diffusion or could be facilitated by a specific export system. Since AcCys is a component of mycothiol, the mycothiol-dependent detoxification of electrophiles requires only a single enzyme, mycothiol S-conjugate amidase, to cleave the S-conjugate and produce the mercapturic acid excreted by the cell.

Other glutathione-producing cells excrete the bimane derivative of glutathione (GSmB) intact. *E. coli* (A. Kaluzna, et al. (1977) *Biochem. Mol. Biol. Int.* 43:161–171), yeast (Z. Li, et al. (1996) *J. Biol. Chem.* 271:6509–6517), plants (E. Martinola, et al. (1993) *Nature* 364:247–249), and cultured mammalian cells (R. P. J. Oude Elferrink, et al. (1993) *Hepatology* 12:434–444, T. Ishikawa, et al. (1994) *J. Biol. Chem.* 269:29085–29093) all excrete GSmB produced within the cell into a vacuole or to the extracellular space using an ATP requiring ABC transporter. Thus, the intracellular degradation of MSmB in mycobacteria represents a marked departure from the pattern found in GSH-producing organisms.

Figure 8:
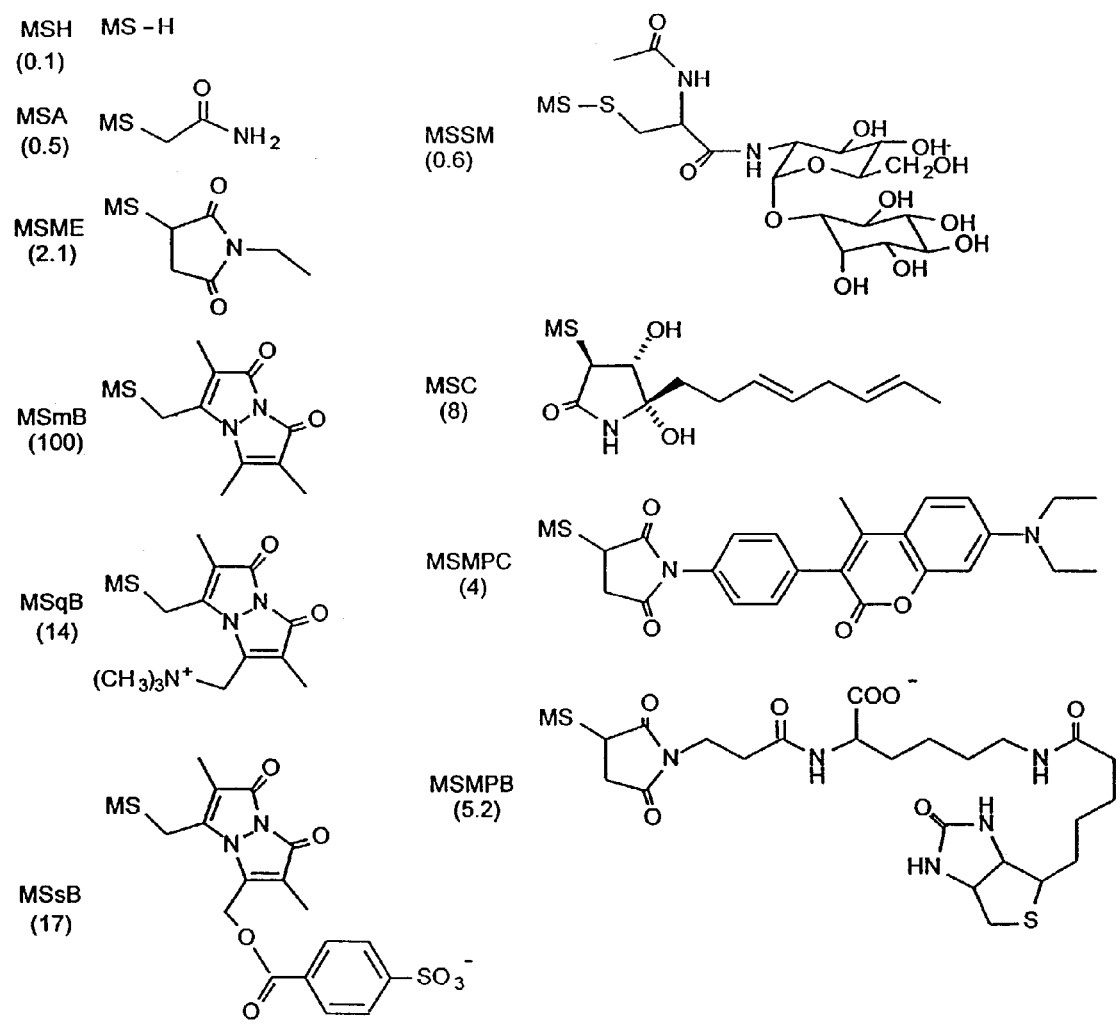
FIG. 8 is a chart showing the chemical structures of various S-conjugate substrates used to test the substrate-specificity of mycothiol S-conjugate amidase as shown in Table 2 herein. The relative activities compared with MSmB taken as 100% are shown in parentheses.

Significant amidase activity was observed for a variety of groups attached to sulfur in the S-conjugate (FIG. 8). Low but measurable activity was obtained with the two carbon acetamido moiety attached to sulfur (FIG. 8, MSA) from reaction with iodoacetamide whereas 4-fold greater activity was measured with an N-ethylsuccinimidyl residue (MSME) produced by reaction with N-ethylmaleimide. However, substantially larger maleimide derivatives (MSMC and MSMPB) exhibited only modestly increased activity. It is evident that invention S-conjugate amidase can accommodate rather large groups attached to the sulfur. Nevertheless, MSmB was the best of the substrates tested and modification of the bimane by attachment of a positively charged trimethylammonio group (MSqB) or a negatively charged p-sulfobenzoyloxy residue (MSsB) led to a 6–7-fold loss of activity (FIG. 8). The only S-conjugate studied that would occur in nature is that derived from cerulenin (MSC), an antibiotic produced by the actinomycete *Cephalosporum cerulens*. (S. Omura, (1981) supra.)

This mycothiol conjugate exhibited 8% of the activity found with MSmB. The S-conjugate structure shown in FIG. 8 was drawn on the assumption that the reaction of cerulenin with mycothiol produces a product analogous to that demonstrated previously for its reaction with cysteine (H. Funabashi, et al. (1989) *J. Biochem.* (Tokyo) 105:751–755). Based upon the finding that MSC is a reasonable substrate for invention S-conjugate amidase, it is believed that invention S-conjugate amidase functions as a component of a mycothiol-dependent detoxification system in mycobacteria which can operate to inactivate bacterial antibiotics. In this regard, it may be significant that an *M. smegmatis* mutant blocked in mycothiol production, and thus lacking the amidase cofactor, was found to have 20-fold increased sensitivity to rifampin (Newton, et al. (1999), supra.).

Invention S-conjugate amidase has little activity with mycothiol or mycothiol disulfide (FIG. 8), which is an essential specificity in order to minimize a futile cycle involving amidase degradation of mycothiol or mycothiol disulfide in combination with mycothiol biosynthesis. Although mycothiol is not a substrate for the amidase, at mM levels it does inhibit amidase activity with MSmB as substrate. The thiol biotinylating reagent 3-(N-maleimidopropionyl)biocytin (MPB) is utilized to capture mycothiol as the MSMPB conjugate in our current immunoassay protocols for determination of mycothiol (M. D. Unson, et al. (1999) *J. Clin. Microbiol.* 37:2153–2157). Since MSMPB is a substrate for invention S-conjugate amidase (Table 2, FIG. 8), it is important that the amidase be inactivated when assaying cells by use of protein denaturing conditions for cell extraction as employed here and in the earlier study (M. D. Unson, et al. (1999) supra.).

The invention family of acyl glucosaminyl inositol amidases is an important practical tool for studies of mycothiol biochemistry because it provides an efficient means for producing GlcN-Ins. GlcN-Ins is required as a substrate for the assay of ATP-dependent cysteine:GlcN-Ins ligase (S. J. Anderberg, et al. (1998) supra., C. Bornemann, et al. (1997) supra.), as a standard for HPLC calibration (S. J. Anderberg, et al. (1998) supra.), and as a precursor of synthetic analogs. Mycothiol is easily isolated from *M. smegmatis* and can be converted quantitatively to MSmB in minutes. Subsequent treatment with purified amidase produces an easily separated mixture of AcCySmB and stereochemically pure α(1 1) GlcN-Ins. This method is much faster and cheaper than the low yield isolation from *Micromonospora echinospora* (S. J. Anderberg, et al. (1998) supra.) or the multi-step chemical synthesis (C. Bornemann, et al. (1997) supra.) previously used to produce GlcN-Ins, which generates isomers of the final compound, only one of which is active.

Additional studies have been conducted to illustrate the use of mycothiol by mycobacteria for detoxification of such toxic compounds as vinyl chloride, 1,2 dibromoethane, and numerous other haloalkanes (Example 9). Assay of the thiol content of *Rhodococcus* sp. Strain AD45 shows that mycothiol is the major thiol, with glutathione as a minor thiol at about 10% of the mycothiol level. Further analysis of the mycothiol S-conjugate amidase activity with mycothiol-bimane derivative as substrate discovered that amidase activity was twice as high as that found in *Mycobacterium smegmatis* (see Example 9, Table 3). The high mycothiol content relative to the glutathione content of this organism along with the inability to saturate the glutathione S-transferase with the substrate glutathione suggests that the enzyme used by mycobacteria to detoxify toxic environmental substances, such as vinyl chloride, 1,2 dibromoethane, numerous other haloalkanes, and the like, is actually a mycothiol S-transferase and not a glutathione S-transferase.

Mycothiol S-conjugate amidase is present in the test organism (at levels higher than found in *M. smegmatis*) and is believed to be involved in the detoxification of the epoxide, isoprene monoxide, formed during the detoxification of isoprene by *Rhodococcus* sp. AD45. An example of a related compound is the antibiotic cerulenin, an epoxide that reacts with mycothiol and is a substrate of mycothiol conjugate amidase derived from *M. smegmatis*, as discussed above.

Thus, in another embodiment, bacteria used (or specifically engineered) to detoxify environmental toxins can be transformed with the subject gene constructs to cause or increase expression of acyl glucosaminyl inositol amidase in the bacteria, thereby increasing the capacity of the bacteria to detoxify environmental toxins or expanding the range of toxins against which the bacteria are effective.

The invention will be further described with reference to the following examples; however, it is to be understood that the invention is not limited to such examples.

EXAMPLE 1

In vitro Enzymatic assays. The enzymatic activity was routinely assayed by quantitation of the bimane (2,3,5,6-tetramethyl-1H,7H-pyrazolo[1,2-a]pyrazole-1,7-dione)derivative of N-acetylcysteine (AcCySmB) produced from the bimane derivative of mycothiol (MSmB), prepared from purified mycothiol (Newton et al., (1995) supra.). Separation of the various modified thiols was performed by high-pressure liquid chromatography (HPLC). A sample (2–10 µL) of extract was mixed with 40 µL of 30 µM MSmB in 3 mM 2-mercaptoethanol, 25 mM N-2-hydroxyethylpiperazine-N'-2-ethanesulfonic acid (HEPES) chloride pH 7.5 and reacted 10–30 mm at 30° C. before quenching the reaction with 50 µL of 40 mM methanesulfonic acid on ice. The mixture was centrifuged for 3 min at 14,000×g in a microcentrifuge at room temperature and the supernatant analyzed by HPLC without dilution. A shortened version (45 min) of HPLC method 1 of Fahey and Newton (R. C. Fahey, et al. (1987) *Methods Enzymol.* 143:85–96) was used for separation of MSmB and AcCySmB. The bimane derivative of mycothiol eluted at 23.5 min and AcCySmB eluted at 27 min.

A preparation of the mycothiol S-conjugate amidase (30–50% saturated ammonium sulfate fraction chromatographed on Sephadex G-75) was used to study the stoichiometry of the reaction. Reaction was initiated by mixing a sample (9 µL, 7 µg total protein) of the preparation of the enzyme with 0.9 mL of 50 mM sodium phosphate, pH 7.5 containing 100 µM MSmB.

For determination of bimane derivatives of thiols, a sample (70 µL) of reaction mixture was removed, mixed with 4 µL 5 M methanesulfonic acid, and analyzed by HPLC without dilution.

For analysis of GlcN-Ins, a sample (2–8 µL) of the reaction mixture was mixed with enough 1M HEPES chloride pH 8 to bring the volume to 10 µl and then with 5 µL acetonitrile and 5 µL of 10 mM AccQ-Fluor reagent (6-aminoquinolyl-N-hydroxysuccinimidyl carbamate, Waters). The mixtures were incubated for 1 min at room temperature followed by 10 min at 60° C., diluted with 60 µL of water, and quantified by HPLC as previously described (S. J. Anderberg, et al. (1998) supra.).

The specificity of the amidase for substrate was assessed by measuring the production of GlcN-Ins in most cases. A sample (5 µL) of 1 mM substrate was mixed with 40 µL of 3 mM 2-mercaptoethanol, 25 mM HEPES chloride, pH 7.5. The reaction was initiated with 5 µL of purified amidase (50-fold diluted stock, 4.4 µg ml$^{-1}$). Triplicate samples were quenched at 0, 10, and 30 min by mixing each sample with 50 µL of acetonitrile containing 5 mM NEM and incubating at 60 C for 10 min. After cooling on ice, the samples were clarified by centrifugation for 15 min at 14000 g. A sample (15 μL) of the supernatant was modified with AccQ-Fluor for amine analysis in a total reaction volume of 125 μL as previously described (S. J. Anderberg, et al. (1998) supra.).

In the substrate specificity tests, activity with 100 μM mycothiol or with the monobromobimane derivative of the compounds shown in Table 2 (chemical structures shown in FIG. 8) was assayed. In these tests, 1-D-myo-inosityl-2-(L-cysteinyl)-amido-2-deoxy-α-D-glucopyranoside (CySmB-GlcN-Ins) or of 2-(N-acetyl-L-cysteinyl)amido-2-deoxy-(α,β)-D-glucopyranoside (AcCySmB-GlcN) was at least $10^3$ lower than with 100 μM MSmB, demonstrating that invention S-conjugate amidase is highly specific for S-conjugates of mycothiol. Conjugates of mycothiol with the antibiotic cerulenin, N-ethylmaleimide, 3-(N-maleimidopropionyl)-biocytin, and 7-diethylamino-3-(4'-maleimidylphenyl)-4-methylcoumarin also exhibited significant activity as shown in Table 2 below:

TABLE 2[a]

| Amidase Substrates | Activity (nmole/min/mg) | Relative Activity (%) |
|---|---|---|
| Mycothiol conjugate with: | | |
| control[b] | 13 ± 11 | 0.29 ± 0.25 |
| mBBr (MSmB) | 4480 ± 870 | (100) |
| sBBr (MSsB) | 740 ± 94 | 17 ± 2 |
| qBBr (MSqB) | 620 ± 44 | 14 ± 1 |
| cerulenin (MSC) | 370 ± 20 | 8.0 ± 0.5 |
| iodoacetamide (MSA) | 21 ± 2 | 0.47 ± 0.04 |
| NEM (MSME) | 107 ± 9 | 2.1 ± 0.2 |
| CPM (MSMPC) | 183 ± 50 | 3.8 ± 1.1 |
| MPB (MSMPB) | 246 ± 12 | 5.2 ± 0.3 |
| Other substrates | | |
| Mycothiol (MSH) | 4 ± 1 | 0.1 |
| Mycothiol disulfide (MSSM) | 25 ± 1 | 0.6 |
| CySmB-GlcN-Ins | <4.5[c] | <0.1 |
| AcCySmB-GlcN | <0.8[d] | <0.02 |

[a]Measuring GlcN-Ins production from 0.1 mM substrate by 0.022 μg purified amidase at 30 C. except as noted.
[b]With 0.1 mM MSmB in the absence of amidase; calculated for 0.022 μg enzyme.
[c]Rate determined from CySmB formation.
[d]Rate determined from AcCySmB formation.

mBBr=monobromobimane; MPB=3-(N-maleimidopropionyl)biocytin; MSA=iodoacetamide S-conjugate of mycothiol; MSC=cerulenin S-conjugate of mycothiol; MSH=mycothiol, 1-D-myo-inosityl-2-(N-acetylcysteinyl)amido-2-deoxy-α-D-glucopyranoside; MSME=NEM S-conjugate of mycothiol; MSMC=CPM S-conjugate of mycothiol; MSMPB=MPB S-conjugate of mycothiol; MSsB=sBBr S-conjugate of mycothiol; MSqB=qBBr S-conjugate of mycothiol; NEM=N-ethylmaleimide; qBBr=monobromotrimethylammoniobimane; sBBr=p-sulfobenzoyloxybromobimane.

EXAMPLE 2

Preparation of GlcN-Ins. Salt free, stereochemically pure GlcN-Ins was prepared from MSmB by enzymatic hydrolysis using partially purified amidase. A sample of MSmB purified by HPLC (4.8 μmoles) was incubated in 2 mL of water without buffer at 23° C. with 15 μg of partially purified amidase. The reaction was monitored hourly for its content of MSmB and AcCySmB and the pH was adjusted to 7.5 with 1M NaOH as necessary. Additional aliquots of enzyme were added as necessary to achieve complete hydrolysis of the MSmB over a maximum interval of 12 h, after which the reaction mixture was acidified to a pH less than 3 with trifluoroacetic acid (Fluka). A 1 mL SepPak, C18 cartridge (Waters) was prepared by sequentially washing with 5 mL of methanol; 5 mL of 50% methanol, 0.1% trifluoroacetic acid in water; and 20 mL 0.1% trifluoroacetic acid in water. The acidified reaction mixture was applied and the column eluted with 0.1% trifluoroacetic acid. Fractions (1 ml) were collected and analyzed for their content of GlcN-Ins. The fractions containing GlcN-Ins were pooled, lyophilized, and resuspended in a small volume of water. Complete hydrolysis of MSmB is important because AcCys-mB and protein, but not MSmB, are retained on the SepPak C18 cartridge under these conditions.

EXAMPLE 3

Analysis of M. smegmatis treated in vivo with mBBr in culture. Since mBBr is known to penetrate cells rapidly and to convert intracellular thiols to their bimane derivatives (Newton, et al. (1995) supra.), the fate of mycothiol in M. smegmatis cells treated with mBBr was examined to ascertain whether the reaction of FIG. 1C occurs in vivo.

A logarithmic phase culture of M. smegmatis was cooled on ice to ~3° C. to reduce enzymatic reactions prior to reaction with 0.5 mM mBBr. Excess reagent was reacted with 2-mercaptoethanol and the cells were pelleted, washed, and resuspended in a small amount of ice cold medium. The cells were diluted with prewarmed medium and replaced in the shaking incubator at 37° C. (time, t=0). Samples were removed and analyzed for intracellular and extracellular mycothiol related compounds over a 4 h interval (FIG. 3).

At t=0 no significant mycothiol or MSmB was found in cells or medium but both contained significant levels of AcCySmB, indicating that the mycothiol had fully reacted with mBBr and hydrolyzed to the corresponding AcCySmB derivative (FIG. 3), much of this conversion presumably having occurred during the initial incubation on ice. At t=0, 90 mmol per 100 mL (3.5 μmol per g RDW) of AcCySmB was present in the cells and 160 mmol per 100 mL was found in the medium. Within 5 min the cellular AcCySmB level had fallen to 8 mmol per 100 mL and the medium level increased to 220 nmol per 100 mL. Subsequent analyses found essentially all of the AcCySmB in the medium at a level of 225–230 nmol per 100 mL, accounting for 80–90% of the original cellular mycothiol content. No MSmB appears to be exported from cells as <1 mmol per 100 mL (<0.5%) was detected in the medium or the cell washes. A logarithmic phase culture (1 L) of M. smegmatis mc²155 ($OD_{600}$=1.2) in 7H9 Middlebrook medium was cooled on ice to 3° C. The iced culture was incubated with mBBr (0.5 mM from a 180 mM stock solution in acetonitrile) for 20 min; excess 2-mercaptoethanol (1.0 mM) was added, and the incubation continued on ice for an additional 10 min. The cells were pelleted by centrifugation and washed twice with 200 mL of sterile, ice-cold 7H9 Middlebrook medium to remove excess bimane derivative of 2-mercaptoethanol. The cells were resuspended in 50 mL of sterile ice cold medium and the experiment was initiated (t=0) by dilution into 950 mL of prewarmed (37° C.) 7H9 Middlebrook medium. The cell suspension was shaken in an incubator (225 rpm, 37° C.) and a "t=0" sample (100 mL) was removed from the culture within one min. This sample was mixed with an equal weight of ice and stored on ice until the second sample was taken similarly at 5 min, after which both were pelleted by centrifugation at 5000 g and 4° C. Additional samples were obtained in this manner at times up to 4 hours. An aliquot (0.5 mL) of supernatant was mixed with 0.5 mL of acetonitrile and incubated at 60° C. for 10 min. After centrifugation the supernatant was assayed by HPLC for bimane-labeled thiols in the medium. The pellet (always iced) was separated into 3 roughly equal parts in 1.5 mL microcentrifuge tubes and extracted for 10 min in 3 ways as follows.

The first sample was extracted using 1 mL of 60° C. acetonitrile-water for determination of cellular thiol-bimane derivatives. The second sample was extracted using 1 mL of 60° C. acetonitrile-water containing 2 mM mBBr and 20 mM tris(hydroxymethyl)aminomethane (Tris) pH 8.0 for determination of the sum of each cellular thiol and thiolbimane derivative. The third sample was extracted using 1 mL of 60 C acetonitrile-water containing 5 mM N-ethylmaleimide (NEM) and 10 mM HEPES chloride pH 7.5. All tubes were centrifuged at 14000 g in a microcentrifuge and the supernatants removed for analysis.

For determination of GlcN-Ins, 0.1 mL was removed from supernatant of the third sample and 15 μL was assayed in a total assay volume of 125 μL as previously described (S. J. Anderberg, et al. (1998) supra.). The remaining 0.9 mL of supernatant of the third sample was derivatized with 2 mM mBBr and 20 mM Tris pH 8.0 to serve as the NEM control for the analysis of sample 2. All assay pellets were dried in a vacuum oven and weighed to obtain the residual dry weight (RDW) for calculation of results.

The cellular level of GlcN-Ins was comparable to that of AcCySmB at t=0 (FIG. 3) and represented a ~25-fold increase above the normal level of ~0.1 μmol GlcN-Ins per g RDW (S. J. Anderberg, et al. (1998) supra.). The GlcN-Ins level declined slowly over the 4 h incubation while the mycothiol content increased from a nearly undetectable level at t=0 to about half the normal cellular level after 4 h (FIG. 3). These results indicate that GlcN-Ins produced by cleavage of MSMB is retained by the cell and is utilized in the resynthesis of mycothiol. No detectable low molecular weight bimane derivatives remained in the cells at 4 h. During the 4 h incubation the $A_{600}$ value initially decreased ~15% but then recovered its initial value of 1.2. Continued incubation at 37 C resulted in a further increase to 1.6 at 8.5 h and a final $A_{600}$~2.6 at 30 h. Thus, at least one cell doubling occurred subsequent to the treatment with mBBr and the cells entered stationary phase at a normal cell density.

EXAMPLE 4

Purification of mycothiol S-conjugate amidase. *M. smegmatis* cells were cultured as above to late log phase, collected by centrifugation at 5000 g, and frozen at −70 C until used. Thawed cell paste (100 gm) was mixed with 500 mL of 3 mM 2-mercaptoethanol, 25 mM HEPES chloride, pH 7.5 (assay buffer) without protease inhibitors and disrupted by sonication on ice. The extract was centrifuged for 30 min at 15000 g at 4 C and the supernatant was mixed with saturated ammonium sulfate to 20% saturation and incubated for 1 h on ice. After centrifugation at 15000 g and 4° C. for 30 min, the pellet was discarded. The supernatant was adjusted to 50% saturated ammonium sulfate, incubated on ice overnight, and centrifuged for 30 min 10000 g at 4 C. The pellet was resolubilized in 60 mL of cold assay buffer and dialyzed against assay buffer overnight at 4 C.

The dialyzed sample was applied to a 1.4×27 cm column of Toyopearl DEAE 650C (TosoHaas) and the column was washed with ~3 column volumes of assay buffer at 4 C. The column was developed with a linear gradient in assay buffer from 0 to 0.4 M NaCl and the amidase activity eluted at ~0.2 M NaCl. The active fractions were pooled and saturated ammonium sulfate was added to 20% saturation. After 1 h on ice the solution was clarified by centrifugation for 30 min at 10000 g and the pellet was discarded. The supernatant was applied to a 1.4×27 cm column of Phenyl Sepharose 4B (Sigma) equilibrated with 20% saturated ammonium sulfate in assay buffer at 4° C. The column was washed with 5 column volumes 20% saturated ammonium sulfate followed by 5 column volumes of 10% saturated ammonium sulfate, both in assay buffer. The Phenyl Sepharose 4B column was eluted in assay buffer with a linear gradient from 10% to 0% saturated ammonium sulfate and the amidase activity eluted at ~1–2% saturated ammonium sulfate. The active fractions were pooled and concentrated at 4 C using a Biomax-50 (Millipore) ultrafilter.

The concentrated activity pool was applied to a Sephadex G-100 (Pharmacia) column (1.8×88 cm) equilibrated with assay buffer. The majority of the activity eluted at an estimated $M_r$ of 36 000. The most active peak fractions were pooled and concentrated on Centricon C-30 (Amicon) ultrafilters at 4 C. Purified amidase was stored in assay buffer containing 20% glycerol at −70° C. for at least 12 months without significant loss of activity.

Results of these experiments to purify the enzyme responsible for cleavage of MSMB from *M. smegmatis* are shown in Table 1 below.

TABLE 1

Purification of *M. smegmatis* mycothiol S-conjugate amidase.

| Purification Step | Protein (mg) | Total Activity[a] (units) | Specific Activity[a] (units/mg) | Yield (%) | Purification Factor |
|---|---|---|---|---|---|
| Crude Extract | 8,700 | 10.6 | 0.0012 | 100 | 1 |
| 20-50% ammonium sulfate pellet | 3,600 | 6.3 | 0.0018 | 59 | 1.5 |
| DEAE 650C | 2,100 | 7.5 | 0.0036 | 71 | 3.0 |
| Phenyl Sepharose | 76 | 9.4 | 0.123 | 89 | 103 |
| Sephadex G-100 | 0.35 | 1.16 | 3.3 | 11 | 2,800 |

[a]Assayed with 30 μM MSmB in assay buffer.

As shown in FIG. 4, the third step in the three step chromatography of the 20–50% saturated ammonium sulfate fraction, the three center fractions eluted from the main peak of the G-100 chromatography had specific activities of ~3,000 nmol/min-mg protein with 30 μM MSmB as substrate and were pooled to provide a pure amidase preparation. This sample produced a single band on SDS gel electrophoresis. Only the peak fractions of activity from the gel filtration step were selected and this was the principle factor in reducing the overall yield to 11% as shown in Table 1 above.

EXAMPLE 5

Characterization of mycothiol S-conjugate amidase. The level of purification and subunit molecular weight was estimated on 12% SDS polyacrylamide slab gel electrophoresis (U. K. Laemmli, (1970) *Nature* 227:680–685) calibrated with broad range standards (Bio-Rad). The native molecular weight was estimated based upon 3 preparative scale chromatographies on Sephadex G-100 used as the final step of purification and described above. The column was calibrated with dextran blue, phosphorylase B, bovine serum albumin, ovalbumin, carbonic anhydrase, trypsin inhibitor, and lysozyme, all from Sigma.

Based on these studies a subunit $M_r$ for the amidase of 36 000 was estimated. A native $M_r$ of 36 000 was determined for the main peak of activity on 3 independent preparative Sephadex G-100 chromatographic separations. This indicates that invention S-conjugate amidase is active as a monomer. A small and variable amount of activity eluted in the void volume (FIG. 3), prior to bovine serum albumin ($M_r$=68 000). Thus, an aggregate larger than a dimer, or a larger protein with related catalytic activity, may be present. The activity from the preceding Phenyl Sepharose step was concentrated using a 50 000 cutoff filter and no activity was found in the filtrate, suggesting that at high protein concentration the enzyme may be aggregated.

A value of $K_m$=95±8 μM and a value of $k_{cat}$=8 s$^{-1}$ was determined for invention S-conjugate amidase with MSmB as substrate (Table 1).

The amino-terminal sequence of the purified *M. smegmatis* amidase was determined on an Applied Biosystems Procise Model 494 gas phase protein sequencer by the UCSD Department of Biology Protein Sequencing Facility. Sequencing of the amino-terminal portion of purified amidase produced an amino-terminal sequence of (M)SELRL-MAVHAHPDDESSKG (SEQ ID NO:2). The first amino acid was not uniquely defined and its assignment was uncertain until later verified as methionine. A BLAST search (Sanger Centre) of the *M. tuberculosis* H37Rv genome database (S. T. Cole, et al. (1998) *Nature* 393:537–544) identified an open reading frame of unknown function, Rv1082, having an identical amino-terminal sequence and a $M_r$ of 32 700. When *M. tuberculosis* Rv1082 gene was used to BLAST search the available databases, open reading frames with identical amino-terminal sequences and very high overall homology were found in genomes of *M. tuberculosis* CSU #93 (TIGR), *M. avium* (TIGR), *M. leprae* (Sanger Centre) and *M. bovis* (Sanger Centre). An alignment of the sequences of five homologs of *M. Smegmatis* mycothiol S-conjugate amidase is shown in FIG. 6.

EXAMPLE 6

Preparation of Mycothiol S-conjugates. Mycothiol S-conjugates were prepared by reaction of excess electrophile with mycothiol followed by removal or reaction of excess electrophile. Stock solutions (100 mM) of electrophile were prepared in acetonitrile (NEM, iodoacetamide; Sigma) or in dimethylsulfoxide [7-diethylamino-3-(4'-maleimidylphenyl)-4-methylcoumarin (CPM, Molecular Probes), 3-(N-maleimidopropionyl)biocytin (MPB, Sigma)]. Reaction with these electrophiles at 2 mM in 25 mM *HEPES chloride pH 7.5 was initiated by addition of mycothiol to 1 mM from a 32 mM stock solution in H$_2$O (pH~3) and was allowed to proceed 15 min in the dark. Excess reagent was removed by extracting 3 times with an equal volume of H$_2$O-saturated dichloromethane. A cerulenin (Sigma) stock solution (100 mM in acetonitrile) was diluted 5-fold in 25 mM HEPES chloride pH 7.5, reacted 15 min with 1 mM mycothiol, and extracted 5 times with H$_2$O-saturated dichloromethane. Prior to extraction a 1 μL aliquot was withdrawn for reaction with mBBr and analysis of residual mycothiol by HPLC. This showed that >99% of the mycothiol had reacted. Stock solutions (50 mM) of p-sulfobenzoyloxybromobimane (sBBr) and monobromotrimethylammoniobimane (qBBr) were prepared in 50% aqueous dimethylsulfoxide and diluted to 2 mM for reaction with 1 mM mycothiol in 25 mM HEPES chloride pH 7.5 for 15 min. Since these charged electrophiles cannot be extracted with dichloromethane, reaction was terminated with excess (1.1 mM) 2-mercaptoethanol. In control studies it was shown that 100 μM levels of these 2-mercaptoethanol derivatives do not inhibit the amidase promoted hydrolysis of MSmB and it was assumed that their presence does not influence the reaction rate with other bimane derivatives of mycothiol.

EXAMPLE 7

Cysteine:GlcN-Ins Ligase assays. The purified *M. smegmatis* amidase was assayed for ATP-dependent cysteine:GlcN-Ins ligase activity essentially as described by Anderberg et al (S. J. Anderberg, et al. (1998) supra). As a positive control, a cell extract was prepared from *M. smegmatis* logarithmic phase cells disrupted by sonication on ice in 3 mM 2-mercaptoethanol in 50 mM HEPES chloride pH 7.5. The cell debris was pelleted by centrifugation at 14000 g for 3 min and the supernatant was dialyzed against 3 mM 2-mercaptoethanol in 50 mM HEPES chloride pH 7.5 overnight at 4° C.

The purified amidase or dialyzed *M. smegmatis* extract was incubated in 100 μM Cysteine, 50 μM GlcN-Ins, 1 mM ATP, 5 mM MgCl$_2$ in 50 mM HEPES chloride pH 7.5 at 30° C. and assayed for the time dependent formation of 1-D-myo-inosityl-2-(L-cysteinyl)amido-2-deoxy-α-D-glucopyranoside (Cys-GlcN-Ins) by HPLC (S. J. Anderberg, et al. (1998) supra.). The reaction was initiated with the addition of the purified amidase (0.044 μg) or cell extract (50 μg protein) and was sampled at 0 and 60 min.

The purified amidase (0.044 μg) gave <0.33 nmol/min/mg Cys-GlcN-Ins at a protein concentration where the amidase reaction rate for 30 μM MSmB was ~3000 nmol/min/mg. As a positive control, the ligase reaction was also assayed for a dialyzed crude extract from *M. smegmatis* and 0.36 nmol/min/mg protein Cys-GlcN-Ins was formed in accord with previous reports (Newton, et al. (1999), supra., S. J. Anderberg, et al. (1998) supra.). Thus, mycothiol S-conjugate amidase does not appear to be involved in mycothiol biosynthesis since it has no significant ability to catalyze ATP-dependent ligation of cysteine with GlcN-Ins. It therefore does not appear to be a bifunctional enzyme analogous to the glutathionylspermidine synthetase/amidase which catalyzes both the biosynthesis and degradation of glutathionylspermidine in *E. coli* (D. S. Kwon, et al.(1997) supra.) and in *Crithidia fasciculata* (E. Tetaud, et al. (1998) supra.).

EXAMPLE 8

Cloning and Expression of *M. tuberculosis* Rv1082.

Bacterial strains, vectors and culture conditions. *M. tuberculosis* H37Rv NCTC 7416 was obtained from the National Collection of Type Cultures, London, United Kingdom. *E. coli* DH5α (Clontech Laboratories, Inc., Palo Alto, Calif.) and *E. coli* BL21 (DE3) (Novagen, R & D) were used for maintenance of plasmids and expression of foreign proteins, respectively. The plasmid pET-22b (Novagen) was used as an expression vector in *E. coli* BL21 (DE3). *E. coli* strains were cultured on Luria-Bertani (LB) agar or broth with or without selective antibiotics. Mycobacterial strains were cultured in Middlebrook 7H9 broth or 7H10 agar (Difco) supplemented with OADC (Difco) Tween 80, and glycerol.

Amplification and cloning of Rv1082. Genomic DNA of *M. tuberculosis* H37Rv was prepared as described previously (Newton, et al. (1999), supra.). The open reading frame Rv 1082 which encodes for the putative amidase was amplified from this DNA with the following primers: 1, 5'-TAGCCATGGTGAGCGAACTGCGGTTGATG-3' (SEQ ID:10); and 2, 5'-GGATCCCGATCCCGGCGAA-CAATTCGGT-3' (SEQ ID:11). Primers 1 and 2 contained NcoI and BamHI restriction sites respectively. PCR was performed with Taq polymerase obtained from Gibco Brl, using 2 mM MgCl$_2$ and 5% Dimethyl sulfoxide (DMSO). Annealing temperatures was 50° C. The PCR products were separated on a 1% agarose gel. The appropriate PCR product was ligated into the vector pCR2.1 of the TA cloning kit (Invitrogen) and transformed into *E. coli* DH5α or INVF'α by standard chemical transformation procedure. Clones containing the vector were selected on LB+ampicillin (100 μg/ml) plates and plasmid DNA was digested with restriction endonucleases NcoI and BamHI (Fermentas). Restriction enzyme-digested plasmids were isolated with a QIAquick gel extraction kit (Qiagen Ltd.). A corresponding digestion was also applied to plasmid pET-22b and the two products were ligated together with T4 DNA ligase to obtain the plasmid pYA1082E (FIG. 2).

Expression and purification of mycothiol S-conjugate amidase. Competent cells of *E. coli* BL21(DE3) were prepared according by the CaCl$_2$ method (30) and were transformed by the heat shock method for 2 min at 42° C. with 100 ng of pYA1082E (FIG. 2). The transformed *E. coli* were then plated onto LB agar supplemented with ampicillin (100 μg/ml). Single colonies were inoculated into 5 ml of LB broth also containing ampicillin (100 μg/ml). After overnight incubation at 37° C. with shaking, the individual cultures were diluted 1:50 in the same medium and incubation was continued at 37° C. with shaking. Isopropyl-β-D-thiogalacto-pyranoside (IPTG) was added to a final concentration of 0.4 mM when the optical density (OD) at 600 nm reached 0.6. Cultures were centrifuged at 5000×g, 15 minutes at room temperature, and pellets were sonicated three times for 30 seconds each. Proteins were separated by centrifugation (15,000×g, 4° C., 15 min) into soluble and insoluble fractions.

Amidase inclusion bodies contained in the insoluble fractions were purified from *E. coli* membrane proteins by centrifugation (45,000×g, 90 minutes, 4° C.). The invention amidase was separated by 7.5% sodium dodecyl sulfate polyacrylamide electrophoresis (SDS-PAGE) and stained with Coomassie blue. N-terminal amino acid sequence was verified after electrophoresis of samples in SDS-PAGE and electroblotting to PVDF membrane. Edman degradation was performed and the sequence of the first five amino acids from the NH$_2$-terminus was determined at the UBC Protein Sequencing Laboratory. In order to obtain soluble protein, Rv 1082 amidase inclusion bodies were resuspended into 1×PBS (pH 7.4) and slowly added drop-wise to solution of 16 M Urea and 2 M DTT to make a final concentration of 8 M Urea and 1 M DTT. Soluble amidase was then dialyzed via a Spectra/P or 8000 cellulose membrane (VWR Scientific) against 200 volumes of 1×TBS (pH 7.4) at 4° C. for 16–24 hours. The sample was then centrifuged for 15 minutes, 4° C.×15,000 g.

Cloning and expression of the *M. tuberculosis* Rv1082 gene. The *M. tuberculosis* Rv1082 gene was cloned and expressed under the control of a T7 promoter in the *E. coli* expression vector pET-22b. Using the primers described in Materials and Methods, Rv1082 open reading frame was successfully amplified by PCR from *M. tuberculosis* H37Rv genomic DNA to give a 858 bp fragment and cloned into the T7 expression vector pET-22b. The map of the resulting plasmid described as pYA1082E is shown in FIG. 2. The mycothiol S-conjugate amidase gene of *M. tuberculosis* was expressed from pYA1082E following treatment of exponentially growing pYA1082E-*E. coli* BL21 (DE3) transformed cells with 1 mM IPTG at room temperature for about 12 hours. As shown by SDS-PAGE and Coomassie blue staining, IPTG induced a protein approximately 37 kDa in size. This expressed band was visible in both whole cell lysates and post-sonication pellet within two hours of IPTG induction. Further purification attempts revealed that mycothiol S-conjugate amidase was present in the form of insoluble inclusion bodies. The inclusion bodies remained as stable insoluble aggregates even following multiple washes with detergent solutions. To verify that the recombinant protein present in the inclusion bodies is identical to the predicted protein encoded by the *M. tuberculosis* mycothiol S-conjugate amidase gene, N-terminal amino acid sequencing on the IPTG-inducible protein we performed. The first five amino acids of this IPTG-induced band were shown to be identical to the amino acid sequence of the Rv1082 gene product derived from the *M. tuberculosis* genome sequence database.

Purification and renaturation of mycothiol S-conjugate amidase from inclusion bodies. The approach taken involved solublization of the inclusion bodies in a highly concentrated urea and DTT solution followed by these values are similar to those obtained for other recombinant proteins that were recovered from inclusion bodies formed in *E. coli* (Landman et al. 1991). Cells were cultured in Luria Bertani broth containing 100 μg/mL ampicillin at 37° C. to OD$_{600}$=0.8 when isopropyl-β-D-thiogalactopyranoside added to 0.4 mM and the culture was shaken overnight at 25° C. Cells were pelleted by centrifugation for 10 min at 5000 g and 4° C., sonicated in 5 volumes of assay buffer on ice, and centrifuged for 5 min at 14000 g at room temperature. About 85% of the amidase activity, using MSmB as substrate, was associated with the pellet fraction which was resuspended and incubated with periodic vortexing for 1 h at 37° C. in 8 M urea containing 20 mM DTT. The suspension was centrifuged for 3 min at 14000 g and the supernatant dialyzed against 100 volumes of 25 mM HEPES chloride pH 7.5 containing 1 mM glutathione disulfide and 2 mM glutathione for 15 h, and then against 100 volumes of 25 mM HEPES chloride pH 7.5 containing 3 mM 2-mercaptoethanol for 4 h. After centrifugation, the supernatant contained soluble amidase activity and was assayed with 0.1 mM mycothiol and 0.1 mM MSmB as described above.

*M. tuberculosis* mycothiol S-conjugate amidase possesses functional mycothiol-S-conjugate amide hydrolase activity. Alkylation of MSH with mBBr produces the fluorescent S-conjugate, MSmB, which can be quantitated by HPLC with fluorescence detection (Newton et al. 1995; Newton et al. 1996). *E coli* has no mycothiol metabolism and is not expected to contain mycothiol conjugate amidase endogenous proteins that would give background to these assays. The amidase activity was found to be associated with the insoluble cell pellet material. Using 0.1 mM MSmB as substrate, the resolublilzed crude protein extract was found to produce 4.1±0.05 nmoles/min/mg protein GlcN-Ins and 5.4±0.3 nmoles/min/mg protein AcCysmB.

Functional and Comparative analysis of mycothiol S-conjugate amidase. To verify the assignment of *M. tuberculosis* Rv1082 as a mycothiol conjugate amidase, extracts from uninduced cells showed <0.01 nmol/min/mg amidase activity with 100 μM MSmB as substrate whereas extracts of cells induced with isopropyl-β-D-thiogalactopyranoside produced 4.1 nmol/min/mg amidase activity. *E. coli*, unlike *M. smegmatis*, does not have mycothiol metabolism (Newton, et al., 1996), which difference accounts for the very low background activity of uninduced cell extract. When these extracts were assayed with 0.1 mM mycothiol as substrate, <0.002 nmol/min/mg amidase activity was observed. Thus, the recombinant *M. tuberculosis* amidase is more than 2000 fold more active with MSmB than with mycothiol itself, a substrate specificity very similar to that of *M. smegmatis* amidase. (Table 2).

The S-conjugate amidase which is encoded by the *M. tuberculosis* open reading frame Rv1082 is 288 amino acid long, slightly negatively charged peptide with a predicted molecular weight of 32699 da and theoretical PI of 5.11.

EXAMPLE 9

In this example, a thiol analysis of *Rhodococcus* sp. Strain AD45 was conducted. The thiol analysis shows that mycothiol is the major thiol, with glutathione as a minor thiol at about 10% of the mycothiol level. Further analysis of the mycothiol S-conjugate amidase from this bacterium showed amidase activity with mycothiol-bimane derivative as substrate was 2-fold higher than that found in *Mycobacterium smegmatis* (Table 3). The high mycothiol content relative to the glutathione content of this organism along with the inability to saturate the glutathione S-transferase with the substrate glutathione suggests that the active amidase in this organism is actually a mycothiol S-transferase and not a glutathione S-transferase. Thus, the mycothiol S-conjugate amidase present in this organism (at levels higher than found in *M. smegmatis*) (Table 3) is believed to be involved in the detoxification of the epoxide, isoprene monoxide, formed during the detoxification of isoprene by *Rhodococcus* sp. AD45. An example of a related compound is the antibiotic cerulenin, an epoxide that reacts with mycothiol and is a substrate of mycothiol conjugate amidase from *M. smegmatis*. Table 3 below shows the thiol content and mycothiol S-conjugate amidase in crude cell extracts of *Rhodococcus* sp. AD45 and *Mycobacterium smegmatis* mc$^2$155.

TABLE 3

| Organism | Thiol Content μMoles/gram residual dry weight | | | Amidase activity |
|---|---|---|---|---|
| | Cysteine | Glutathione | Mycothiol | Units/mg protein |
| *Rhodococcus* sp. AD45 | 0.31 | 1.1 | 12.6 | 0.0025 |
| *M smegmatis* mc$^2$155[a] | 0.16 | <0.001 | 10.6 | 0.0012 |

[a]G.L. Newton et al., Biochem.Biophys. Res. Comm. 255:239–244 (1999).

These findings illustrate that, in the case of mycobacteria, mycothiol is the major low molecular weight thiol and will form a mycothiol conjugate. The product of this conjugation may still be toxic and is a substrate for the mycothiol conjugate amidase. Reaction of the mycothiol conjugate with a mycothiol conjugate amidase enables the excretion of the detoxified conjugate as a mercapturic acid. Therefore, mycothiol and mycothiol S-conjugate amidase are involved in and can be used for detoxification of halogenated hydrocarbons and other environmental toxins.

Accordingly, in another embodiment according to the present invention, there are provided methods for detoxifying a toxic substance by contacting the toxic substance with an acyl glucosaminyl inositol amidase. In a preferred embodiment, bacteria transformed with a polynucleotide encoding an invention amidase polypeptide, or a variant thereof, is used to express the amidase in situ under environmental conditions and the toxic substance is an environmental pollutant, such as a halogenated hydrocarbon, hydrocarbon, or other petroleum derivative.

While the invention has been described in detail with reference to certain preferred embodiments thereof, it will be understood that modifications and variations are within the spirit and scope of that which is described and claimed.

That which is claimed is:

1. A method for decreasing the antibiotic-resistance of pathogenic acyl glucosaminyl inositol amidase-producing actinomycetes, wherein the first 20 amino acids from the N-terminus of a mycothiol S-conjugate amidase comprise an amino acid sequence having at least 80% sequence identity to SEQ ID NO: 2, said method comprising: contacting the actinomycetes with an inhibitor of acyl glucosaminyl inositol amidase activity, wherein the inhibitor is mycothiol, wherein the intracellular presence of the inhibitor decreases activity of the amidase, thereby decreasing the antibiotic resistance of the actinomycetes as compared with untreated controls, and wherein when the actinomycetes is contacted with 3-(bromomethyl)-2,5,6-trimethyl-1H,7H-pyrazolo[1,2-a]pyrazole-1,7-dione (monobromobimane [mBBr]) in the absence of the inhibitor, the actinomycetes converts mBBr into a mercapturic acid, which acid is exported from the actinomycetes.

2. The method of claim 1, wherein the inhibitor inhibits intracellular amidase activity of the amidase.

3. The method of claim 1, wherein the actinomycetes are pathogenic actinomycetes selected from *M. smegmatis, M. Tuberculosis, M. leprae, M. Bovis, M. intracellulare, M. africanum, M. marinarum, M. chelonai, Corynebacterium diphtheria, Actinomyces israelii*, or *M. avium*.

4. The method of claim 1, wherein the actinomycetes encode the amidase within an antibiotic biosynthetic operon.

* * * * *

UNITED STATES PATENT AND TRADEMARK OFFICE
CERTIFICATE OF CORRECTION

PATENT NO. : 7,183,094 B2 Page 1 of 1
APPLICATION NO. : 10/427218
DATED : February 27, 2007
INVENTOR(S) : Newton et al.

It is certified that error appears in the above-identified patent and that said Letters Patent is hereby corrected as shown below:

COLUMN 1, LINE 14
Add the following title and paragraph beginning on Line 14 of Column 1 prior to the paragraph entitled "FIELD OF THE INVENTION", specifically:

--GRANT INFORMATION

This invention was made in part with government support under Grant Nos. AA11393 and TW00976 awarded by the National Institutes of Health. The government has certain rights in this invention.--

Signed and Sealed this

Third Day of July, 2007

JON W. DUDAS
*Director of the United States Patent and Trademark Office*